United States Patent [19]

Nagase et al.

[11] Patent Number: 4,843,100
[45] Date of Patent: * Jun. 27, 1989

[54] BENZOYLUREAS, THEIR PRODUCTION AND USE

[75] Inventors: Hiroshi Nagase, Kawanishi; Yasuo Sato, Kyoto, both of Japan

[73] Assignee: Takeda Chemical Industries, Ltd., Osaka, Japan

[*] Notice: The portion of the term of this patent subsequent to Dec. 30, 2003 has been disclaimed.

[21] Appl. No.: 63,749

[22] Filed: Jun. 19, 1987

Related U.S. Application Data

[63] Continuation of Ser. No. 706,164, Feb. 27, 1985, abandoned.

[30] Foreign Application Priority Data

Feb. 27, 1984 [JP] Japan ................... 59-36881

[51] Int. Cl.$^4$ ............... C07C 147/14; C07C 147/12; A01N 47/34
[52] U.S. Cl. ............................ 514/594; 564/44
[58] Field of Search ............... 564/23, 44; 514/584, 514/594

[56] References Cited

U.S. PATENT DOCUMENTS

| | | | |
|---|---|---|---|
| 4,013,717 | 3/1977 | Wellinga et al. | 564/44 |
| 4,276,310 | 6/1981 | Sirrenberg et al. | 564/23 |
| 4,277,499 | 7/1981 | Sirrenberg et al. | 564/44 |
| 4,399,152 | 8/1983 | Brouwer et al. | 424/322 |
| 4,468,405 | 8/1984 | Rigterink et al. | 564/44 |
| 4,533,676 | 8/1985 | Sirrenberg et al. | 564/44 |
| 4,632,938 | 12/1986 | Nagase et al. | 564/44 X |

FOREIGN PATENT DOCUMENTS 71279 2/1983 European Pat. Off. .

Primary Examiner—Charles F. Warren
Assistant Examiner—Carolyn S. Greason
Attorney, Agent, or Firm—Wenderoth, Lind & Ponack

[57] ABSTRACT

This invention relates to a benzoylurea derivative of the formula:

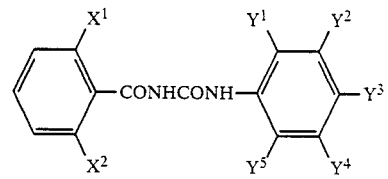

wherein $X^1$ and $X^2$ are hydrogen, halogen, alkyl or alkoxy; and one of $Y^1$, $Y^2$, $Y^3$, $Y^4$ and $Y^5$ is halogenoalkylsulfinyl or halogenoalkylsulfonyl, and the others are hydrogen, halogen or alkyl, exhibiting excellent insecticidal and ovicidal activities (particularly, molt inhibitory activity), their production and use.

5 Claims, No Drawings

BENZOYLUREAS, THEIR PRODUCTION AND USE

This application is a continuation of now abandoned application Ser. No. 706,164, filed Feb. 27, 1985.

The present invention relates to benzoylurea derivatives of the formula:

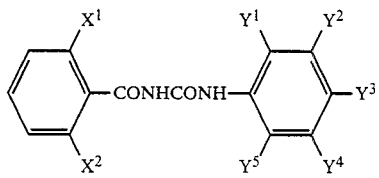

wherein $X^1$ and $X^2$ are hydrogen, halogen, alkyl or alkoxy; and one of $Y^1$, $Y^2$, $Y^3$, $Y^4$ and $Y^5$ is halogenoalkylsulfinyl or halogenoalkylsulfonyl, and the others are hydrogen, halogen or alkyl, which possess excellent insecticidal activity, to processes for producing the same, and to insecticides containing the same.

N-(2,6-Dihalogenobenzoyl)-N'-(substituted-phenyl-)urea derivatives have heretofore been known as one of benzoylurea derivatives (e.g., British Pat. Nos. 1324293 and 1501607, U.S. Pat. No. 4,277,499, European Patent Publication Nos. 71279 and 88343, etc.), but no benzoylurea compound having halogenoalkylsulfinyl or halogenoalkylsulfonyl as a substituent for the substituted phenyl group has been known so far. Out of these conventionally known benzoylurea derivatives, also, one exhibiting satisfactory insecticidal effect has not yet been found.

The present inventors, under these circumstances, conducted extensive research, and as a result, succeeded in synthesizing novel benzoylurea derivatives of the formula [I] by oxidizing a compound of the formula:

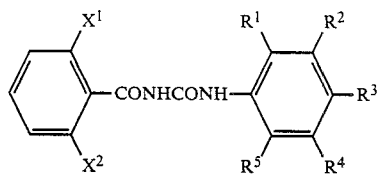

wherein $X^1$ and $X^2$ are as defined hereinbefore; and one of $R^1$, $R^2$, $R^3$, $R^4$ and $R^5$ is halogenoalkylthio or halogenoalkylsulfinyl, and the others are hydrogen, halogen or alkyl, or reacting a compound of the formula:

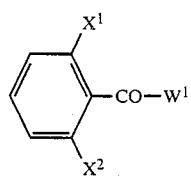

with a compound of the formula:

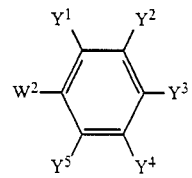

wherein $X^1$, $X^2$, $Y^1$, $Y^2$, $Y^3$, $Y^4$ and $Y^5$ are as defined hereinbefore; and one of $W^1$ and $W^2$ is —N=C=O (isocyanato) and the other is amino. The inventors also found that the derivatives [I] unexpectedly exhibit insecticidal and ovicidal activities (particularly, molt inhibitory activity) superior to those of known compounds having analogous structures and also are of lessened toxicities toward mammal and fishes, thus finding application as a safe insecticide exerting less adverse effects on the environment.

Thus, the present invention relates to:

(1) Benzoylurea derivatives [I], (2) A process for producing the benzoylurea derivatives [I], characterized in that said process comprises oxidizing a compound of the formula:

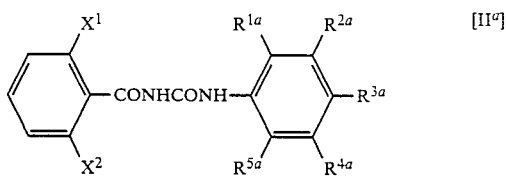

wherein $X^1$ and $X^2$ are as defined hereinbefore; and one of $R^{1a}$, $R^{2a}$, $R^{3a}$, $R^{4a}$ and $R^{5a}$ is halogenalkylthio, and the others are hydrogen, halogen or alkyl, (3) A process for producing benzoylurea derivatives of the formula:

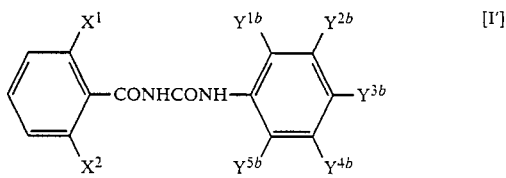

wherein $X^1$ and $X^2$ are as defined hereinbefore; and one of $Y^{1b}$, $Y^{2b}$, $Y^{3b}$, $Y^{4b}$ and $Y^{5b}$ is halogenoalkylsulfonyl, and the others are hydrogen, halogen or alkyl, characterized in that said process comprises oxidizing a compound of the formula:

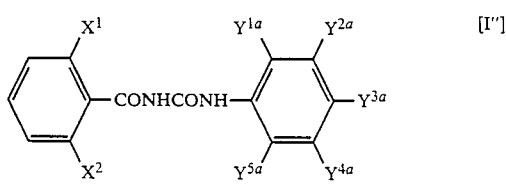

wherein $X^1$ and $X^2$ are as defined hereinbefore; and one of $Y^{1a}$, $Y^{2a}$, $Y^{3a}$, $Y^{4a}$ and $Y^{5a}$ is halogenoalkylsulfinyl, and the others are hydrogen, halogen or alkyl, (4) A process for producing the benzoylurea derivatives [I], characterized in that said process comprises reacting a compound of the formula:

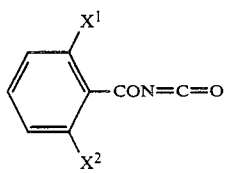

[IV]

wherein $X^1$ and $X^2$ are as defined hereinbefore, with a compound of the formula:

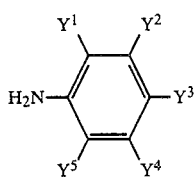

[V]

wherein $Y^1$, $Y^2$, $Y^3$, $Y^4$ and $Y^5$ are as defined hereinbefore, (5) A process for producing the benzoylurea derivatives [I], characterized in that said process comprises reacting a compound of the formula:

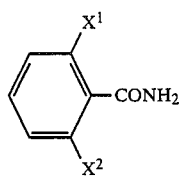

[VI]

wherein $X^1$ and $X^2$ are as defined hereinbefore, with a compound of the formula:

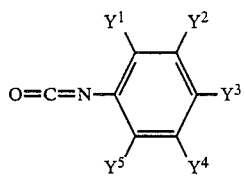

[VII]

wherein $Y^1$, $Y^2$, $Y^3$, $Y^4$ and $Y^5$ are as defined hereinbefore, (6) Insecticidal compositions characteristically featured by containing the benzoylurea derivatives [I].

In the above formulae, $X^1$ and $X^2$ are the same or diffrent, and represent hydrogen, halogen, alkyl or alkoxy. As the halogen represented by $X^1$ and $X^2$, there are used, for example, Cl, Br, F and I. As the alkyl represented by $X^1$ and $X^2$, there are used, for example, straight-chain or branched-chin alkyl of 1 to 4 carbon atoms, such as methyl, ethyl, propyl, isopropyl, butyl, isobutyl, sec-butyl and t-butyl. As the alkoxy represented by $X^1$ and $X^2$, there are used, for example, straight-chain or branched-chain alkoxy of 1 to 4 carbon atoms, such as methoxy, ethoxy, propoxy, isopropoxy, butoxy, isobutoxy, sec-butoxy and t-butoxy. As preferable examples of $X^1$ and $X^2$, there are used, for example, hydrogen, F and Cl. Furthermore, one of $Y^1$, $Y^2$, $Y^3$, $Y^4$ and $Y^5$ is halogenoalkylsulfinyl or halogenoalkyl-sulfonyl, and the other are hydrogen, halogen or alkyl. One of $R^1$, $R^2$, $R^3$, $R^4$ and $R^5$ is halogenoalkylthio or halogenoalkylsulfinyl, and the others are hydrogen, halogen or alkyl. One of $R^{1a}$, $R^{2a}$, $R^{3a}$, $R^{4a}$ and $R^{5a}$ is halogenoalkylthio, and the others are hydrogen, halogen or alkyl. One of $Y^{1a}$, $Y^{2a}$, $Y^{3a}$, $Y^{4a}$ and $Y^{5a}$ is halogenoalkylsulfinyl, and the others are hydrogen, halogen or alkyl. One of $Y^{1b}$, $Y^{2b}$, $Y^{3b}$, $Y^{4b}$ and $Y^{5b}$ is halogenoalkylsulfonyl, and the others are hydrogen, halogen or alkyl. As the halogenoalkylsulfinyl represented by $Y^1$, $Y^2$, $Y^3$, $Y^4$ and $Y^5$, $Y^{1a}$, $Y^{2a}$, $Y^{3a}$, $Y^{4a}$ and $Y^{5a}$, or $R^1$, $R^2$, $R^3$, $R^4$ and $R^5$, there are used, for example, straight-chain or branched-chain alkylsulfinyl of 1 to 4 carbon atoms (preferably, 2 carbon atoms), such as methylsulfinyl, ethylsulfinyl, propylsulfinyl, isopropylsulfinyl, butylsulfinyl, isobutylsulfinyl, sec-butylsulfinyl and t-butylsulfinyl, which are substituted by 1 to 9 halogens (preferably, 2 to 5 halogens) selected from Cl, Br, F and I. Representative examples of such halogenoalkylsulfinyl are, for example, groups represented by the formula $-SOCF_2R$ (wherein R is hydrogen or straight-chain alkyl of 1 to 3 carbon atoms substituted by halogen or halogens as mentioned above), and specifically, there are used, for example, $-SOCHF_2$, $-SOCF_2CF_3$, $-SOCF_2CCl_3$, $-SOCF_2CBr_3$, $-SOCF_2CI_3$, $-SOCF_2CF_2Cl$, $-SOCF_2CF_2Br$, $-SOCF_2CF_2I$, $-SOCF_2CFCl_2$, $-SOCF_2CFBr_2$, $-SOCF_2CFI_2$, $-SOCF_2CFClBr$, $-SOCF_2CFClI$, $-SOCF_2CCl_2Br$, $-SOCFCClBr_2$, $-SOCF_2CHF_2$, $-SOCF_2CHFCl$, $-SOCF_2CHCII$, $-SOCF_2CHFBr$, $-SOCF_2CHClBr$, $-SOCF_2CHCl_2$, $-SOCF_2CHBr_2$, $-SOCF_2CHI_2$, $-SOCF_2CH_2F$, $-SOCF_2CH_2Cl$, $-SOCF_2CH_2Br$, $-SOCF_2CH_2I$ and $-SOCF_2CH_3$. As the preferable halogenoalkylsulfinyl, there are used, for example, $-SOCF_2CF_3$, $-SOCF_2CHF_2$, $-SOCF_2CHFCl$, $-SOCF_2CHFBr$, and $-SOCF_2CHCl_2$. As the halogenoalkylsulfonyl represented by $Y^1$, $Y^2$, $Y^3$, $Y^4$ and $Y^5$ or $Y^{1b}$, $Y^{2b}$, $Y^{3b}$, $Y^{4b}$ and $Y^{5b}$, there are used, for example, straight-chain or branched-chain alkylsulfonyl of 1 to 4 carbon atoms (preferably, 2 carbon atoms), such as methylsulfonyl, ethylsulfonyl, propylsulfonyl, isopropylsulfonyl, butylsulfonyl, isobutylsulfonyl, sec-butylsulfonyl and t-butylsulfonyl, which are substituted by 1 to 9 halogens (preferably, 2 to 5 halogens) selected from Cl, Br, F and I. Representative examples of such halogenoalkylsulfonyl are, for example, groups represented by the formula $-SO_2CF_2R$ (wherein R is as defined hereinbefore), and specifically, there are used, for example, $-SO_2CHF_2$, $-SO_2CF_2CF_3$, $-SO_2CF_2CCl_3$, $-SO_2CF_2CBr_3$, $-SO_2CF_2CI_3$, $-SO_2CF_2CF_2Cl$, $-SO_2CF_2CF_2Br$, $-SO_2CF_2CF_2I$, $-SO_2CF_2CFCl_2$, $-SO_2CF_2CFBr_2$, $-SO_2CF_2CFI_2$, $-SO_2CF_2CFClBr$, $-SO_2CF_2CFClI$, $-SO_2CF_2CCl_2Br$, $-SO_2CF_2CClBr_2$, $-SO_2CF_2CHF_2$, $-SO_2CF_2CHFCl$, $-SO_2CF_2CHCII$, $-SO_2CF_2CHFBr$, $-SO_2CF_2CHClBr$, $-SO_2CF_2CHCl_2$, $-SO_2CF_2CHBr_2$, $-SO_2CF_2CHI_2$, $-SO_2CF_2CH_2F$, $-SO_2CF_2CH_2Cl$, $-SO_2CF_2CH_2Br$, $-SO_2CF_2CH_2I$, and $-SO_2CF_2CH_3$. As the preferable halogenoalkylsulfonyl, there are used, for example, $-SO_2CF_2CF_3$, $-SO_2CF_2CHF_2$, $-SO_2CF_2CHFCl$, $-SO_2CF_2CHFBr$ and $-SO_2CF_2CHCl_2$. As the halogenoalkylthio represented by $R^1$, $R^2$, $R^3$, $R^4$ and $R^5$ or $R^{1a}$, $R^{2a}$, $R^{3a}$, $R^{4a}$ and $R^{5a}$, there are used, for example, straight-chain or branched-chain alkylthio of 1 to 4 carbon atoms (preferably, 2 carbon atoms), such as methylthio, ethylthio, propylthio, isopropylthio, butylthio, isobutylthio, sec-butylthio and t-butylthio, which are substituted by 1 to 9 halogens (preferably, 2 to 5 halogens) selected from Cl, Br, F and I. Representative examples of such halogenoalkylthio includes, for example, groups represented by the formula $-SCF_2R$ (wherein R is as defined hereinbefore), and specifically, there are used, for example, —SCHF$_2$, —SCF$_2$CF$_3$, —SCF$_2$CCl$_3$, —SCF$_2$CBr$_3$, —SCF$_2$CI$_3$, —SCF$_2$CF$_2$Cl, —SCF$_2$CF$_2$Br, —SCF$_2$CF$_2$I, —SCF$_2$CFCl$_2$, —SCF$_2$CFBr$_2$, —SCF$_2$CFI$_2$, —SCF$_2$CFClBr, —SCF$_2$CFClI, —SCF$_2$CCl$_2$Br, —SCF$_2$CClBr$_2$, —SCF$_2$CHF$_2$, —SCF$_2$CHFCl, —SCF$_2$CHClI, —SCF$_2$CHFBr, —SCF$_2$CHClBr, —SCF$_2$CHCl$_2$, —SCF$_2$CHBr$_2$, —SCF$_2$CHI$_2$, —SCF$_2$CH$_2$F, —SCF$_2$CH$_2$Cl, —SCF$_2$CH$_2$Br, —SCF$_2$CH$_2$I and —SCF$_2$CH$_3$. As the preferable halogenoalkylthio, there are used, for example —SCF$_2$CF$_3$, —SCF$_2$CHF$_2$, —SCF$_2$CHFCl, —SCF$_2$CHFBr and —SCF$_2$CHCl$_2$. As the halogen or alkyl represented by $Y^1$, $Y^2$, $Y^3$, $Y^4$ and $Y^5$, $Y^{1a}$, $Y^{2a}$, $Y^{3a}$, $Y^{4a}$ and $Y^{5a}$, $Y^{1b}$, $Y^{2b}$, $Y^{3b}$, $Y^{4b}$ and $Y^{5b}$, $R^1$, $R^2$, $R^3$, $R^4$ and $R^5$ or $R^{1a}$, $R^{2a}$, $R^{3a}$, $R^{4a}$ and $R^{5a}$, there are used for example those as mentioned for $X^1$ and $X^2$, and preferably, there are employed, for example, hydrogen, F, Cl and methyl.

Representative examples of the benzoylurea derivatives [I] or the objective products of this invention include, for example, compounds represented by the formula:

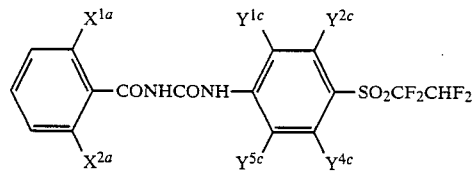

wherein $X^{1a}$ is hydrogen, F or Cl; $X^{2a}$ is Cl or F; $Y^{1c}$ is hydrogen, Br, Cl, F or methyl; $Y^{2c}$ is hydrogen, methyl or Cl; $Y^{4c}$ is hydrogen, methyl or Cl; and $Y^{5c}$ is hydrogen or F, compounds represented by the formula:

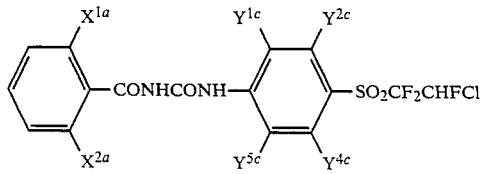

wherein $X^{1a}$, $X^{2a}$, $Y^{1c}$, $Y^{2c}$, $Y^{4c}$ and $Y^{5c}$ are as defined hereinbefore, compounds represented by the formula:

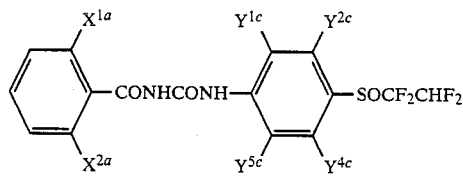

wherein the symbols are as defined hereinbefore, compounds represented by the formula:

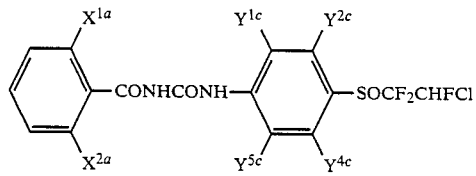

wherein the symbols are as defined hereinbefore, compounds represented by the formula:

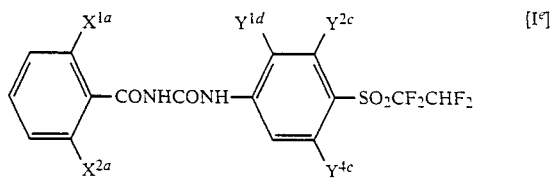

wherein $X^{1a}$, $X^{2a}$, $Y^{2c}$ and $Y^{4c}$ are as defined hereinbefore; and $Y^{1d}$ is F, Cl, Br or methyl, compounds represented by the formula:

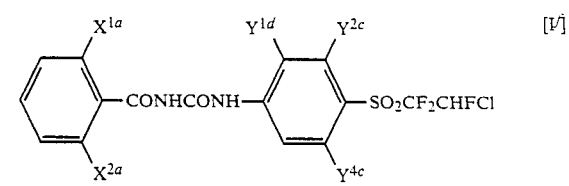

wherein the symbols are as defined hereinbefore, compounds represented by the formula:

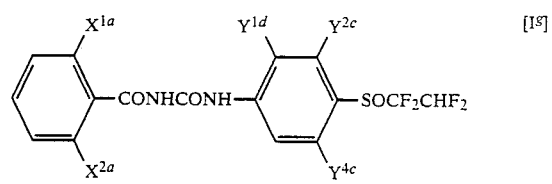

wherein the symbols are as defined hereinbefore, and compounds represented by the formula:

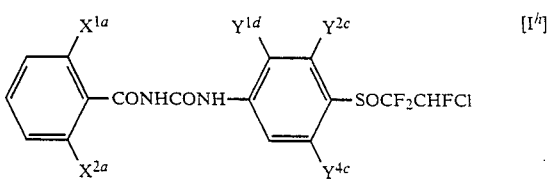

wherein the symbols are as defined hereinbefore. As the preferable benzoylurea derivatives [I], particularly, there are used, for example, compounds represented by the formula:

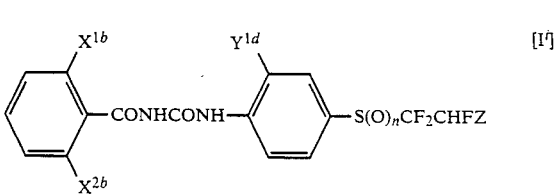

wherein n is 1 or 2; $X^{1b}$ is F or Cl; $X^{2b}$ is F or Cl, when $X^{1b}$ is F, or $X^{2b}$ is hydrogen or Cl, when $X^{1b}$ is Cl; $Y^{1d}$ is as defined hereinbefore; and Z is F or Cl, compounds represented by the formula:

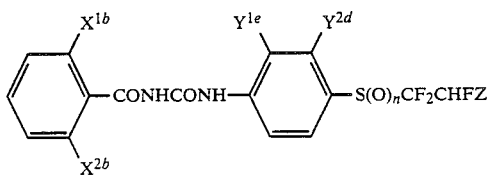

[I$^j$]

wherein n, X$^{1b}$, X$^{2b}$ and Z are as defined hereinbefore; Y$^{1e}$ is hydrogen, Br, Cl or methyl; and Y$^{2d}$ is Cl or methyl, and compounds of the formula:

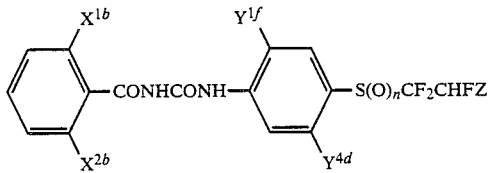

[I$^k$]

wherein n, X$^{1b}$, X$^{2b}$ and Z are as defined hereinbefore; Y$^{1f}$ is Cl or methyl; and Y$^{4d}$ is Cl or methyl.

The objective products [I] of the present invention can exist as isomers, when an asymmetric carbon atom is present in the halogenoalkylsulfinyl or halogenoalkylsulfonyl as represented by Y$^1$, Y$^2$, Y$^3$, and Y$^5$, and may consist of individual isomers or a mixture thereof.

The benzoylurea derivatives [I] of the present invention possess enhanced insecticidal and ovicidal effects and can produce adequate insecticidal and ovicidal effects in less used amount, as compared with known, analogous compounds. Besides offering the economical advantage that the applied amount can be reduced, the benzoylurea derivatives [I] of the present invention are exceedingly low in toxicity toward mammals and also low in fish toxicity, with less adverse effects on the environment, and are therefore effective for exterminating household insect pests, harmful insects parasitic on animals and plants, and forest insect pests. They demonstrate powerfully insecticidal activity, particularly molt inhibitory activity against larvae, by allowing insect pests to directly contact, or ingest, the compounds [I], for example, applying them directly on animals and plants parasitized with insect pests. In addition, they inhibit ovicidal and sterilizing activities and the like, thus enabling more effective control of insect pests to be carried out. Also, the compounds [I] of the present invention, with their reduced phytotoxicity and lowered fish toxicity, provide combined characteristics of safety and advantage in utilizing as an agent for exterminating and preventing hatching of forest insect pests and harmful insects to crops.

The compounds [I] of the present invention and insecticidal preparations containing them are effective for exterminating and preventing hatching of, for example, insect pests of the order Lepidoptera, such as *Spodoptera litura, Plutella xylostella, Pieris rapae crucivora, Chilo suppressalis, Plusia nigrisigna Halicoverpa assulta, Pseudaletia separata, Mamestra brassicae, Adoxophyes orana, Pleuroptya derogata, Cnaphalocrocis medinalis, Phthorimaea operculella, Hyphautria cunea* and *Lymantria dispar;* insect pests of the order Coleoptera, such as *Henosepilachna Vigintioctopunctata, Aulacophora femoralis, Phyllotreta striolata, Oulema oryzae, Echinocnemus squameus, Leptinotorsa decemlineata, Lissorhoptrus oryzophilus* and *Anthonomus grandis;* insect pests of the order Diptera, such as *Musca domestica, Culex pipiens pallens, Tabanus trigonus, Hylemya antiqua* and *Hylemya platura;* insect pests of the order Orthoptera, such as *Locusta migratoria* and *Gryllotalpa africana;* insect pests of Dictioptera, such as *Blattella germanica* and *Periplaneta fuliginosa;* insect pests of the order Isoptera, such as *Reticulitermes speratus;* and nematodes, such as *Aphelenchoides besseyi.*

In utilizing the benzoylurea derivatives [I] of the present invention as in insecticide, such derivatives are formulated into the application forms which general agricultural chemicals can take; namely, one or more of the compounds [I], depending upon the purpose of application, are dissolved or dispersed in a suitable liquid carrier, or mixed or adsorbed with an appropriate solid carrier to process them into the desired forms of preparations, such as emulsifiable concentrate (emulsion), oil or solvent solution, wettable powder, powder, granule, tablet, spray and ointment. As the preferable forms of preparations, there are used, for example, emulsifiable concentrate, wettable powder, powder and granule. These preparations can be prepared, if desired, in accordance with per se known methods by adding, for example, emulsifying agents, suspending agents, spreaders, penetrants, wetting agents, tackifiers and stabilizers.

The proportion of the benzoylurea derivatives [I] contained in the insecticidal composition of the present invention, for example, is suitably in the range of 5 to 90 weight % in the case of emulsifiable concentrate and wettable powder, being appropriately in the region of 0.1 to 10 weight % in the case of oil or solvent preparation and powder, and is suitably in the range of 1 to 20 weight % in the case of granule, varying with the purpose of use, and these concentrations may be suitably altered according to the purpose of application. In applying the emulsifiable concentrate and wettable powder, for example, it is recommendable to dilute and extend (e.g., to 100 to 100000 times the original volume) them properly with water and the like.

Suitable examples of the liquid carrier which is used in the preparation of the insecticidal composition of the present invention include solvents, such as water, alcohols (e.g., methyl alcohol, ethyl alcohol, ethylene glycol, etc.), ketones (e.g., acetone, methyl ethyl ketone, etc.), ether (e.g., dioxane, tetrahydrofurane, cellosolve, etc.), aliphatic hydrocarbons (e.g., gasoline, kerosene, light oil, fuel oil, machine oil, etc.), aromatic hydrocarbons (e.g., benzene, toluene, xylene, solvent naphtha, methylnaphthalene, etc.), halogenated hydrocarbons (e.g., chloroform, carbon tetrachloride, etc.), acid amides (e.g., dimethylformamide, dimethylacetamide, etc.), esters (e.g., ethyl acetate, butyl acetate, mono-, di- or triglycerol esters of lower fatty acids of 2 to 6 carbon atoms, etc.), and nitriles (e.g., acetonitrile, etc.), and these are used in one kind or as a mixture of not less than 2 kinds thereof. The proportion of the liquid carrier contained in the insecticidal composition of the present invention varies depending upon the form of preparations and may, for example, range from 5 to 90 weight %, preferably from 5 to 50 weight %, in the case of emulsifiable concentrate. As the solid carrier, there are used vegetable powders (e.g., soybean meal, tobacco meal, wheat flour, wood flour, etc.), mineral powders (e.g., clays, such as kaolin, bentonite and acid clay, talcs, such as stealite powder and pencil stone or pagodite powder, silicas, such as diatomaceous earth and mica powder, etc.), and furthermore alumina, powdered sulfur, activated carbon, and the like, and these are used in one kind or as a mixture of not less than two kinds thereof. The proportion of the solid carrier contained in the insecticidal composition of the present invention varies depending upon the form of preparations and may, for example, range from 10 to 98 weight %, preferably from 10 to 50 weight %, in the case of wettable powder, powder and granule.

As the ointment base to be used in formulating the insecticidal composition of the present invention into ointment, there can be suitably selected, for example, polyethylene glycol [H(OCH$_2$CH$_2$)$_n$OH wherein n is about 4 to 14], pectin, polyhydric alcohol esters of higher fatty acids (having 10 to 20 carbon atoms) such as mono-, di- or tri glycerol esters of stearic acid, cellulose derivatives such as methylcellulose, sodium arginate, bentonite, higher alcohols, polyhydric alcohols such as glycerol, petrolatum, white petrolatum, liquid paraffin, lard, all kinds of vegetable oils, lanolin, dehydrated lanolin, hardened oil and resins, in one kind, as a mixture of not less than two kinds or as an admixture thereof with a variety of surface active agents, etc. The proportion of the ointment base contained in the insecticidal composition of the present invention may range from 50 to 95 weight %, preferably from 70 to 90 weight %.

As the surface active agent which is used, for example, as an emulsifier, spreader, penetrant or dispersing agent, in preparing the insecticidal composition of the present invention, there may be employed, if desired, soaps, polyoxyalkylaryl esters (e.g., Nonal ®, produced by Takemoto Oils & Fats Co. of Japan, etc.), alkyl sulfates (e.g., Emarum 10 ® and Emaru 40 ®, produced by Kao-Atlas Co. of Japan, etc.), alkyl sulfonates (e.g., Neogen ® and Neogen T ®, produced by Dai-ichi Kogyo seiyaku Co. of Japan, and: Neopelex ®, produced by Kao-Atlas Co. of Japan, etc.), polyethylene glycol ethers (e.g., Nonipol 85 ®, Nonipol 100 ® and Nonipol 160 ®, produced by Sanyo Chemical industries of Japan, etc.), polyhydric alcohol esters (e.g., Tween 20 ® and Tween 80 ®, produced by Kao-Atlas Co. of Japan, etc.) and the like. The proportion of these surface active agents contained in the insecticidal composition of the present invention varies depending upon the form of preparations, and may, for example, range from 1 to 20 weight %, preferably from 3 to 10 weight %, in the case of emulsifiable concentrate; from 3 to 30 weight %, preferably from 5 to 20 weight %, in the case of wettable powder; and from 0.01 to 10 weight % preferably from 0.1 to 5 weight %, in the case of powder and granule.

Also, it is possible to apply mixtures formed by formulating the compound of the present invention suitably with, for example, other kinds of insecticides (e.g., pyrethrin insecticides, organic phosphate insecticides, carbamate insecticides, natural insecticides, etc.), acaricides, nematicides, herbicides, plant hormones, plant growth regulators, fungicides and bactericides (e.g., fungicides and bactericides based on copper, chlorinated hydrocarbons, organic sulfur compounds and phenol compounds, etc.), synergists, attractants, repellents, colorants, and fertilizers, to such an extent as may not adversely affect the insecticidal effect produced by the benzoylurea derivatives [I] of the present invention.

The insecticidal composition of the present invention can be used in the same manner as ordinary insecticidal compositions, for example, by treatment of seedling culture boxes, spraying the stems and leaves of crops, spraying living insect bodies, underwater application in paddy fields and soil treatment. In such cases, the amount used can be varied over a wide range according to the time of application, location of application, method of application, etc., but it is generally desirable to conduct application in such a way that the active ingredient may range from 10 to 2000 g, preferably 50 to 1000 g per hectare.

Concretely, application is carried out by diluting an emulsifiable concentrate of the present invention formed by the mixing of 15 to 25 weight % of N-(2,6-difluorobenzoyl)-N'-[2-fluoro-4-(1,1,2,2-tetrafluoroethylsulfonyl)phenyl]urea or the object product of the present application, 70 to 80 weight % of dimethylformamide as a liquid carrier and 3 to 10 weight % of polyoxyethylene glycol ether (Nonipol 85 ®) as a surface active agent, with water containing 0.01 to 0.05 weight % of Dain ® or a spreader to a concentration of 2 to 20 ppm and spraying the resulting aqueous solution to a place infested with *Spodoptera litura* at a rate of 0.1 to 5 g as an active ingredient per are.

The object product [I] of the present invention is obtained by oxidizing the compound [II$^a$].

The oxidation reaction of the compound as represented by the formula [II$^a$] is desirably conducted in a suitable solvent. The reaction may be conducted in inert solvent, e.g., aliphatic and aromatic hydrocarbons, such as pentane, hexane, heptane, cyclohexane, petroleum ether, petroleum benzine, benzene, toluene and xylene; halogenated hydrocarbons, such as dichloromethane, chloroform, carbon tetrachloride and dichlorobenzene; ethers, such as ethyl ether, dioxane and tetrahydrofurane; nitriles, such as acetonitrile; carboxylic acids, such as formic acid, acetic acid and propionic acid; halogenated carboxylic acids, such as chloroacetic acid and trifluoroacetic acid; esters, such as ethyl acetate; nitro compounds, such as nitrobenzene; ketones, such as acetone, methyl ethyl ketone and methyl isobutyl ketone; amides, such as dimethylformamide, dimethylacetamide and N-methylpyrolidone; sulfones, such as dimethylsulfone and diphenylsulfone; alcohols, such as methanol and ethanol; water or mixtures thereof, and as the preferable solvent, there are used, for example, dichloromethane, chloroform, acetic acid, propionic acid, trifluoroacetic acid, acetone, toluene and water. As the oxidizing agent, there are employed, for example, organic peracids, such as peracetic acid, perbenzoic acid, perphthalic acid and m-chloroperbenzoic acid; peroxides, such as hydrogen peroxide and alkyl hydroperoxides; nitrogen oxides, such as dinitrogen tetraoxide and nitric acid; halogens, such as chlorine, bromine and iodine; halogen compounds, such as hypochlorous acid, hypobromous acid, periodic acid, tert-butylhypochlorite, iodosylbenzene acetate, and iodobenzene dichloride; oxygen compounds, such as ozone, singlet oxygen and superoxides; and metal oxides, such as potassium permanganate, anhydrous chromic acid, osmium tetraoxide, ruthenium tetraoxide, potassium dichromate, lead tetraacetate and manganese dioxide. As the preferable oxidizing agent, there are used, for example, hydrogen peroxide, peracetic acid, m-chloroperbenzoic acid and nitric acid. The amount of the oxidizing agent to be used is not limited so far as it will not interfere with the present reaction, and may normally be 1 to 5 equivalent moles per mole of the compound [II$^a$], preferably 1.2 to 2 equivalent moles. As the reaction temperature, there may be employed temperatures from about 0° to 150° C., preferably thoe from 10° C. to 100° C. The reaction time may be in the range of 5 minutes to 48 hours, but the reaction can normally be terminated after a length of time in the range of 30 minutes to 8 hours. The termination of the reaction can be confirmed by thin-layer chromatography and the like.

In this oxidation reaction, a compound of the formula [I″] is in the first place produced, and [I″] is furthermore oxidized to form a compound of the formula [I′]. Therefore, suitable selection of the oxidizing agent, reaction conditions and the like can yield [I″] or [I′] solely. When a mixture of [I″] and [I′] is formed in the oxidation reaction of [II$^a$], both compounds can be isolated and purified by use of a suitable known separation and purification method.

Among the compounds [I] of the present invention, therefore, the compound of the formula [I′] can be produced by oxidizing the compound of the formula [I″].

Thus, this reaction is desirably carried out in a suitable solvent. The reaction may be conducted in inert solvents, for example, aliphatic and aromatic hydrocarbons, such as pentane, hexane, heptane, cyclohexane, petroleum ether, petroleum benzine, benzene, toluene and xylene; halogenated hydrocarbons, such as dichloromethane, chloroform, carbon tetrachloride and dichlorobenzene; ethers, such as ethyl ether, dioxane and tetrahydrofurane; nitriles, such as acetonitrile; carboxylic acids, such as formic acid, acetic acid and propionic acid; halogenated carboxylic acids, such as chloroacetic acid and trifluoroacetic acid; esters, such as ethyl acetate; nitro compounds, such as nitrobenzene; ketones, such as acetone, methyl ethyl ketone and methyl isobutyl ketone; amides, such as dimethylacetamide and N-methylpyrolidone; sulfones, such as dimethylsulfone and diphenylsulfone; alcohols, such as methanol and ethanol; water or a mixture thereof. As the preferable solvent, there are used, for example, dichloromethane, chloroform, acetic acid, propionic acid, trifluoroacetic acid, acetone, toluene and water. As the oxidizing agent, there are used, for example, organic peracids, such as peracetic acid, perbenzoic acid, perphthalic acid and m-chloroperbenzoic acid; peroxides, such as hydrogen peroxide and alkyl hydroperoxides; halogen compounds, such as periodic acid; and metal oxides, such as anhydrous chromic acid. As the preferable oxidizing agent, there are used, for example, hydrogen peroxide, m-chloroperbenzoic acid and peracetic acid. The amount of the oxidizing agent to be used varies depending for example upon the starting material, oxidizing agent and solvent to be used, and may be 1 to 5 equivalent moles per mole of the starting material [I″], preferably 1.2 to 2 equivalent moles. As the reaction temperature, there may be employed those of about 0° to 150° C., preferably those of 25° to 100° C. The reaction time may be in the range of 5 minutes to 48 hours, but the reaction may be normally terminated within a period of time in the range of 30 minutes to 8 hours. The termination of the reaction can be confirmed by thin-layer chromatography and the like.

In addition, the compound [I] of the present invention can be produced by the reaction of the compound [IV] with the compound [V]. In this reaction, the compound [IV] may be used in the proportion of 1 to 1.2 moles per mole of the compound [VI]. The reaction is desirably carried out in a suitable solvent. The reaction may be conducted in inert solvent, for example, aliphatic and aromatic hydrocarbons, such as pentane, hexane, heptane, cyclohexane, petroleum ether, petroleum benzine, benzene, toluene and xylene; halogenated hydrocarbons, such as dichloromethane, chloroform, carbon tetrachloride and dichlorobenzene; ethers, such as ethyl ether, dioxane and tetrahydrofurane; nitriles, such as acetonitrile; and esters, such as ethyl acetate. As the preferable solvent, there are used, for example, toluene, hexane, acetonitrile, dichloromethane, carbon tetrachloride and dioxane. The reaction temperature may be in the range of from about 0° to about 120° C., preferably from about 10° to 50° C. The reaction time may be in the range of 5 minutes to 24 hours, but the reaction may be normally terminated within a period of time in the range of 20 minutes to 2 hours. The termination of the reaction can be confirmed by thin-layer chromatography, and the like.

Furthermore, the compound [I] of the present invention can be produced by the reaction of the compound [VI] with the compound [VII]. The compound [VII] may be used in the proportion of 1 to 1.2 moles per mole of the compound [VI]. Normally, the reaction is desirably carried out in a suitable solvent. The reaction may be conducted in inert solvent, for example, aliphatic and aromatic hydrocarbons, such as pentane, hexane, heptane, cyclohexane, petroleum ether, petroleum benzine, benzene, toluene and xylene; halogenated hydrocarbons, such as dichloromethane, chloroform, carbon tetrachloride and dichlorobenzene; ethers, such as ethyl ether, dioxane and tetrahydrofurane; nitriles, such as acetonitrile; and esters, such as ethyl acetate. As the preferable solvent, there are used, for example, xylene, dichlorobenzene, and tetrahydrofurane. The reaction temperature may range from about 30° to 150° C., preferably from about 50° to 150° C. The reaction time may be in the range of about 30 minutes to 48 hours, but the reaction may normally be terminated within a period of time in the range of 1 to 24 hours. The termination of the reaction can be confirmed by thin-layer chromatography and the like.

The compound [I] of the present invention thus obtained can be isolated and purified from the reaction mixture by per se known means, such as crystallization, recrystallization, precipitation, extraction, concentration and chromatography.

The starting compound [II$^a$], which is used in the production of the object product[I] of this application, can be produced, for example, by the methods, or methods analogous thereto, as described in British Pat. No. 1501607, U.S. Pat. No. 4,277,499 and European patent publication No. 71279, or the method of reacting the compound [IV] with a compound of the formula:

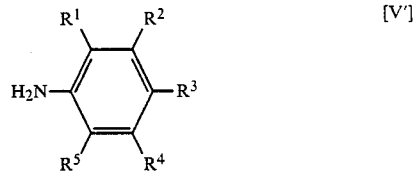

wherein the symbols are as defined hereinbefore. In the reaction of the compound [IV] with the compound [V′], the compound [IV] is used in the proportion in the range of 1 to 1.2 moles per mole of the compound [V′]. Normally, the reaction is desirably carried out in a suitable solvent, and may be conducted in inert solvent, for example, aliphatic and aromatic hydrocarbons, such as pentane, hexane, heptane, cyclohexane, petroleum ether, petroleum benzine, benzene, toluene and xylene; halogenated hydrocarbons, such as dichloromethane, chloroform, carbon tetrachloride and dichlorobenzene; ethers, such as ethyl ether, dioxane and tetrahydrofurane; nitriles, such as acetonitrile; and esters, such as ethyl acetate. The reaction temperatures may generally range from about 0° to about 120° C., preferably from about 10° to 50° C. As to the reaction time, the reaction proceeds over a period in the range of 5 minutes to 24 hours, but may be normally terminated within a length of period in the range of 20 minutes to 2 hours. The termination of the reaction can be confirmed by thin-layer chromatography and the like. The resulting compound [II$^a$] can be isolated and purified by the known means as described above. The compound [IV] can be produced, for example, by the methods, or methods analogous thereto, as described in J. Org. Chem., 27, 3742 (1962), ibid., 30, 4306 (1965), etc. The compound [V'] can be produced, for example, by the methods, or methods analogous thereto, as described in J. Am. Chem. Soc., 82, 5116 (1960) and J. Org. Chem., 29, 895(1964).

Also, the starting compound [V] can be synthesized, for example, by the method as described in J. Org. Chem., 29, 895–898 (1964) and the method as shown in the reaction formulae to be described below.

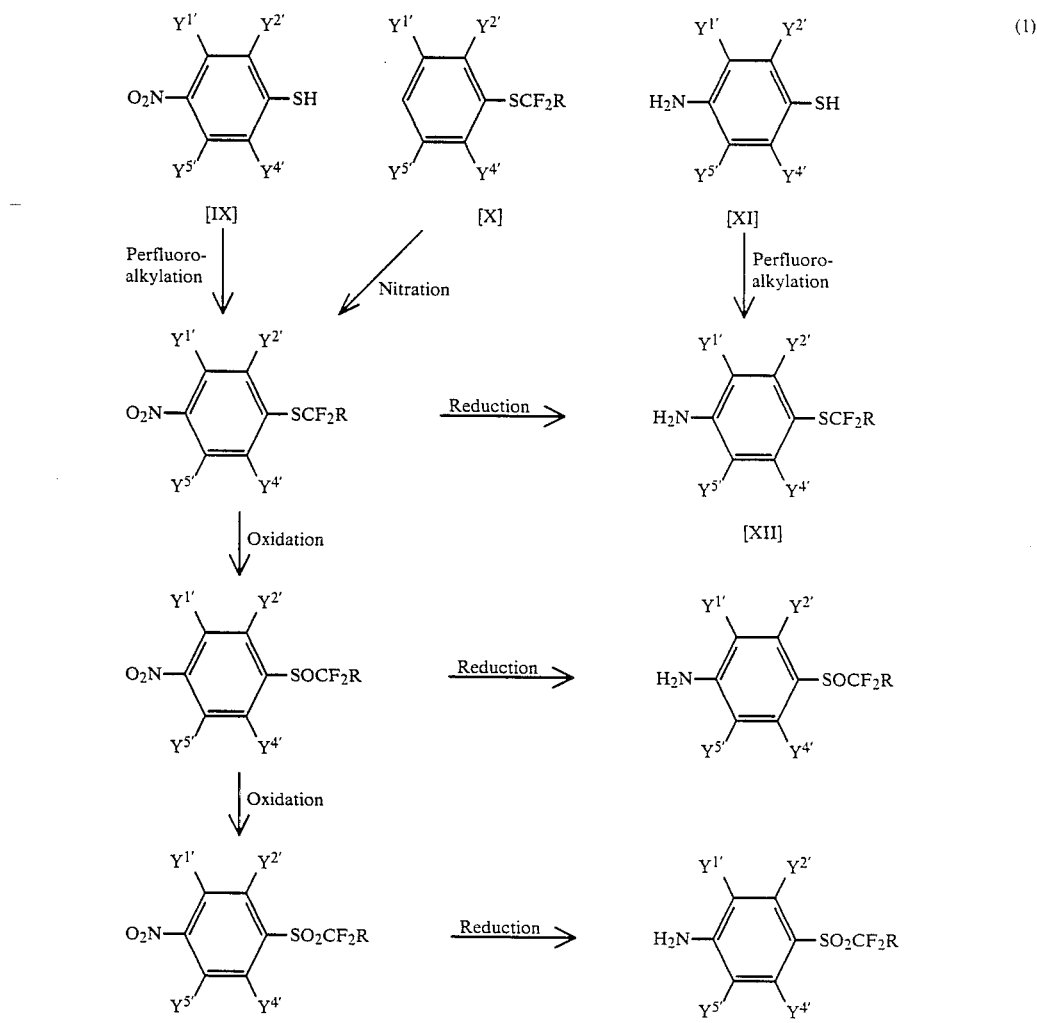

-continued
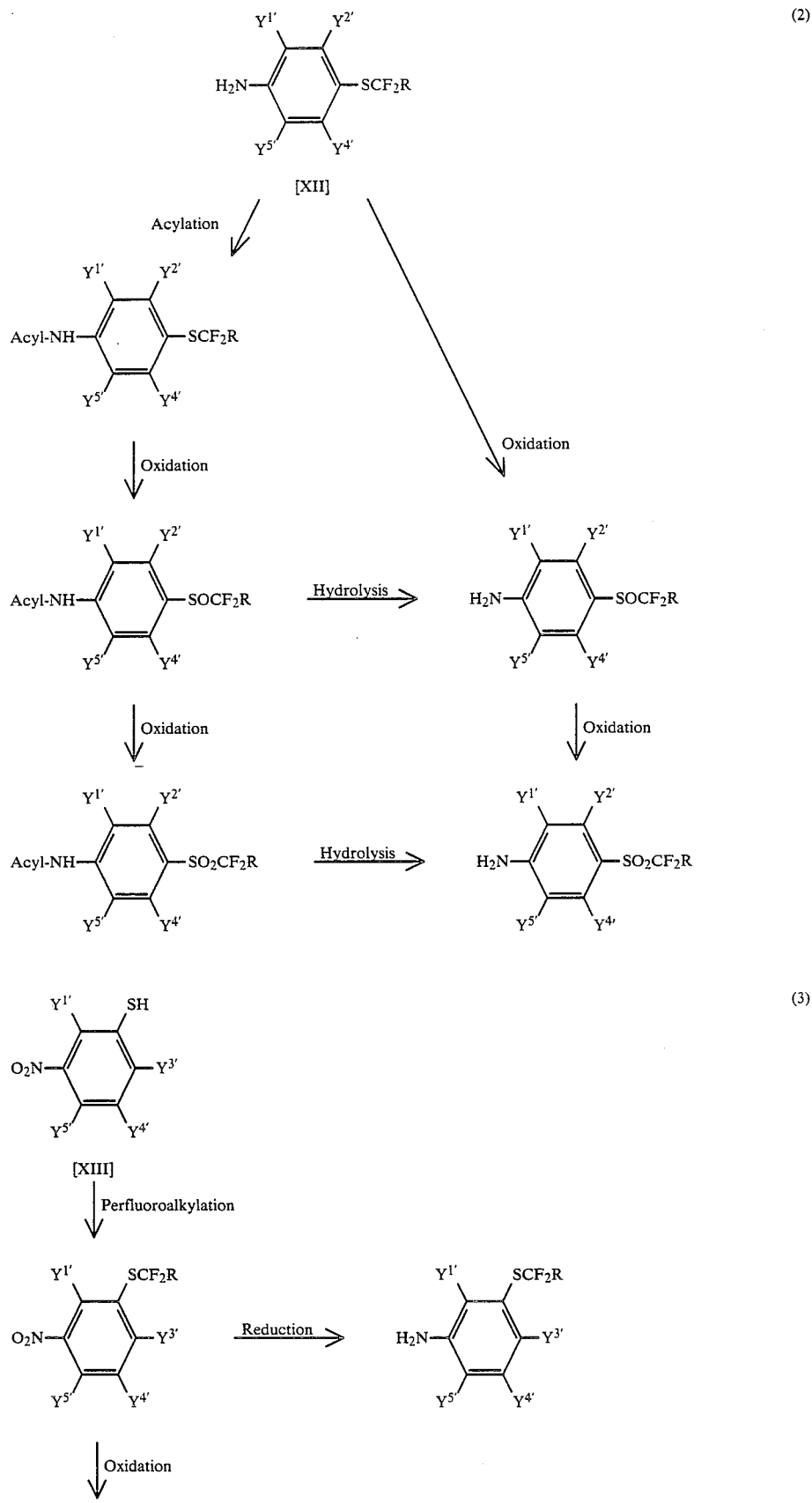

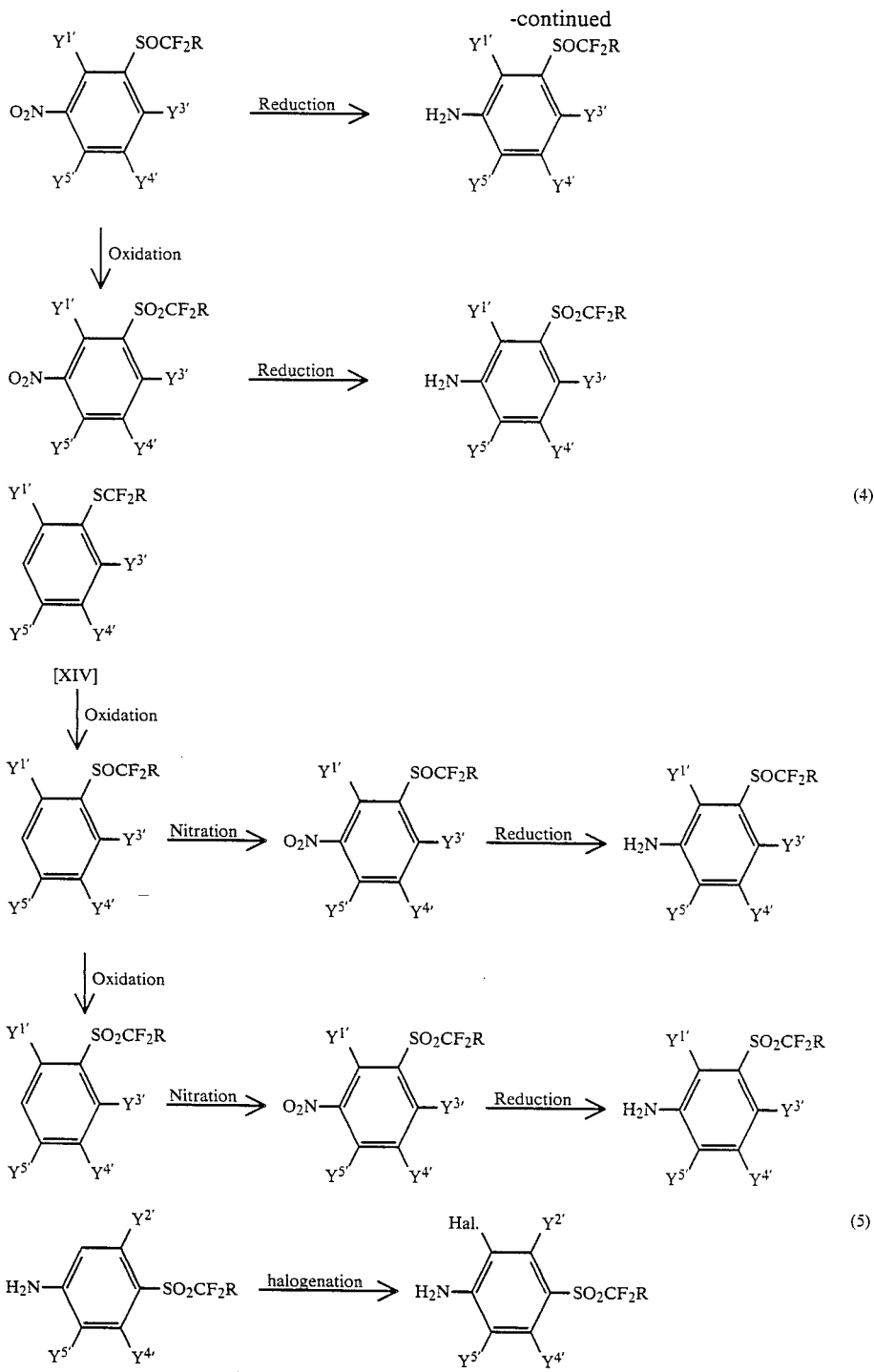

(4)

(5)

wherein $Y^{1'}$, $Y^{2'}$, $Y^{3'}$, $Y^{4'}$ and $Y^{5'}$ are hydrogen, halogen or alkyl; R is as defined hereinbefore; Hal. is halogen; and Acyl is an acyl group.

The starting materials [IX], [X], [XI], [XIII] and [XIV] in the above-mentioned methods (1) through (4) can be obtained, for example, by the methods, or methods analogous thereto, as described in Beilstein' Handbuch der Organischen Chemie', 6, 339; ibid., 13, 397 and 553; and J. Gen. Chem. USSR, 39, 2011–2016 (1969).

Furthermore, the compound [VI] can be produced, for example, by the methods, or methods analogous thereto, as described in J. Med. Chem., 11, 814 (1963) and Beilstein 'Handbuch der Organischen Chemie', 9, 336. The compound [VII] can be produced, for example, by reacting the compound [V] with phosgene in a manner analogous to the known methods.

The reference examples, examples and test examples are described in the following to illustrate the present invention more specifically, but it is to be understood that the present invention shall not be limited by them. The symbols used in Reference Examples, Examples and Test Examples have the following meanings.

| | |
|---|---|
| ml | milliliter |
| g | gram |
| l | liter |
| Me | methyl |
| % | (weight) percent |
| m.p. | melting point |
| b.p. | boiling point |
| ppm | part(s) per million |
| kg | kilogram |
| cm | centimeter |
| Comp'd | Compound |

REFERENCE EXAMPLE 1

To 550 ml of methanol were added 111 g of 2-fluoroaniline and 240 g of sodium thiocyanate, and the mixture was cooled to 0° C. A cooled (0° C.) solution of 176 g of bromine in 500 ml of methanol saturated with sodium bromide was added dropwise to the mixture, with stirring, over the period of 1 hour 15 minutes, during which cooling was effected to maintain the internal temperature at not more than 3° C. After the addition of bromine was completed, the reaction mixture was poured in 2 l of cold water, and 100 g of sodium hydrogencarbonate was added to make the mixture weakly alkaline. The crystals, which separated out, were recovered by filtration and washed with cold water to give 144.5 g of crude 2-fluoro-4-thiocyanatoaniline.

REFERENCE EXAMPLE 2

To a mixed solution consisting of 200 ml of conc. sulfuric acid and 50 ml of ethanol was added 50 g of crude 2-fluoro-4-thiocynatoaniline, and the mixture was heated under reflux for 8 hours. The crystals, which separated out upon standing overnight, were recovered by filtration, and dried in a desiccator to give 44 g of crude 2-fluoro-4-mercaptoaniline hydrochloride. 44 g of crude-2-fluoro-4-mercaptoaniline hydrochloride was suspended in 100 ml of dioxane, and 30 g of triethylamine was added to the suspension. Tetrafluoroethylene was passed into the obtained mixture over the period of 1.5 hours under heating with stirring at 50° to 60° C. (Tetrafluoroethylene was generated by reacting 40 ml of 1,2-dibromotetrafluoroethane with 100 g of powdered zinc in methanol in accordance with the conventional method). After the conclusion of the reaction, the reaction mixture was diluted with water, followed by extraction with two 100 ml portions of dichloromethane. The dichloromethane extract was dehydrated with anhydrous magnesium sulfate, and concentrated to dryness under reduced pressure to give 42.1 g of a yellow oily material. The oily material was distilled under reduced pressure to yield 29.5 g of 2-fluoro-4-(1,1,2,2-tetrafluoroethylthio)aniline as a colorless liquid having a boiling point of 70°-72° C./0.6 mmHg.

By the procedures analogous to the above Reference Examples, the 4-(1,1,2,2-tetrafluoroethylthio)aniline derivatives as shown in the below Table were synthesized. The results are tabulated in Table 1.

TABLE 1

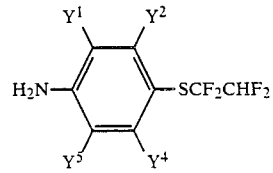

| $Y^1$ | $Y^2$ | $Y^4$ | $Y^5$ | Boiling point(melting point) °C. |
|---|---|---|---|---|
| H | H | H | H | 97–99/1–2 mmHg |
| Me | H | H | H | 90–91/0.3 mmHg |
| H | F | H | H | 81–82/0.1–0.2 mmHg |
| H | Cl | H | H | 113–115/0.3 mmHg |
| H | Me | H | H | 97–100/0.2 mmHg |
| Cl | H | Cl | H | (56–56.5) |
| Cl | Cl | H | H | 122–125/0.3 mmHg |
| H | Cl | Cl | H | 130–131/0.3 mmHg |
| F | H | Cl | H | 92–93/0.15 mmHg |
| Cl | H | H | H | 84–86/0.2 mmHg |
| Br | H | H | H | 105–106/0.5 mmHg |
| Me | Me | H | H | 122/1.5 mmHg |
| Me | H | Me | H | 125/1.5 mmHg |
| Me | H | Cl | H | 115–121/1–2 mmHg |

REFERENCE EXAMPLE 3

In 20 ml of dimethylformamide was dissolved 12.0 g of 2-fluoro-4-mercaptoaniline, and 8.5 g of triethylamine was added to the solution. Trifluorochloroethylene was passed into the mixture over the period of 25 minutes under heating with stirring at 50° to 60° C. (Trifluorochloroethylene was generated by reacting 31 g of 1,1,2-trifluoro-trichloroethane with 90 g of powdered zinc in ethanol in accordance with the conventional method). After the conclusion of the reaction, the reaction mixture was diluted with water, followed by extraction with toluene. The toluene layer was washed with water, 10% NaOH and water successively in the mentioned order, dehydrated with anhydrous magnesium sulfate and concentrated to dryness under reduced pressure to give 17.5 g of a brownish oil material. The oily material was distilled under reduced pressure to yield 13.7 g of 2-fluoro-4-(1,1,2-trifluoro-2-chloroethylthio)aniline as a colorless liquid having a boiling point of 95°–98° C./0.2 mmHg.

By the similar procedure, the 4-(1,1,2-trifluoro-2-chloroethylthio)aniline derivatives as shown in the below Table were synthesized. The results are tabulated in Table 2.

TABLE 2

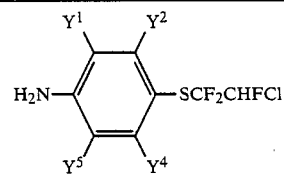

| $Y^1$ | $Y^2$ | $Y^4$ | $Y^5$ | Boiling Point, °C. |
|---|---|---|---|---|
| H | H | H | H | 106–110/0.5 mmHg |
| Cl | H | Cl | H | 124–126/0.15 mmHg |
| Cl | Cl | H | H | 128–130/0.2–0.3 mmHg |
| Cl | H | H | H | 108–109/0.3 mmHg |
| Me | H | H | H | 117–118/0.6 mmHg |
| Br | H | H | H | 113–135/1.0 mmHg |
| Me | Me | H | H | 140/1.5 mmHg |
| Me | H | Me | H | 125/0.6 mmHg |
| Me | H | Cl | H | Oily material (the acetyl derivative shows a melting point of 133–134° C.) |

REFERENCE EXAMPLE 4

A 1.8 g quantity of 2,6-difluorobenzoyl isocyanate was added dropwise to a solution of 2.6 g of 2-fluoro-4-(1,1,2-trifluoro-2-chloroethylthio)aniline in 15 ml of toluene at room temperature (20° to 25° C.). After the reaction was allowed to proceed at the same temperature for 1 hour, the crystals which separated out were recovered by filtration and washed with toluene to give 3.6 g of N-(2,6-difluorobenzoyl)-N'-[2-fluoro-4-(1,1,2-trifluoro-2-chloroethylthio)phenyl]urea, m.p. of 172°-173° C.

By the similar procedure, the compounds as shown in the below Table were synthesized. The results are tabulated in Table 3.

TABLE 3

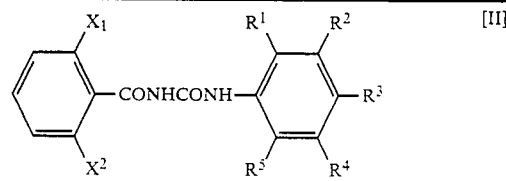

[II]

| $X^1$ | $X^2$ | $R^1$ | $R^2$ | $R^3$ | $R^4$ | $R^5$ | Melting point, °C. |
|---|---|---|---|---|---|---|---|
| F | F | H | H | —SCF$_2$CHF$_2$ | H | H | 197–198 |
| " | Cl | " | " | " | " | " | 190–192.5 |
| Cl | " | " | " | " | " | " | 213–215 |
| " | H | " | " | " | " | " | 175–175.5 |
| F | F | F | " | " | " | " | 177–179 |
| " | Cl | " | " | " | " | " | 195–196.5 |
| Cl | " | " | " | " | " | " | 228–230 |
| " | H | " | " | " | " | " | 152–153.5 |
| F | F | Cl | " | " | " | " | 145 |
| Cl | H | " | " | " | " | " | 130–131 |
| F | F | Me | " | " | " | " | 141–142 |
| F | F | H | Cl | —SCF$_2$CHF$_2$ | H | H | 186–187 |
| Cl | H | " | " | " | " | " | 202–203 |
| F | F | " | Me | " | " | " | 191–192 |
| " | " | H | Cl | " | " | Cl | 189–190 |
| Cl | H | " | " | " | " | " | 182 |
| F | F | Cl | Cl | " | " | " | 153–153.5 (2/5 CHCl$_3$)* |
| Cl | H | " | " | " | " | " | 187–189 |
| F | F | H | Cl | " | " | F | 179–180 |
| Cl | H | " | " | " | " | " | 194–195 |
| F | F | " | H | —SCF$_2$CHFCl | " | H | 202–203 |
| " | Cl | " | " | " | " | " | 187–189 |
| Cl | " | " | " | " | " | " | 207–208 |
| " | H | " | " | " | " | " | 172–173 |
| F | F | F | " | " | " | " | 172–173 |
| Cl | H | " | " | " | " | " | 150–151 |
| F | F | H | Cl | " | " | Cl | 181–183 (1/10 CHCl$_3$)* |
| Cl | H | " | " | " | " | " | 162–163 (1/5 CHCl$_3$)* |
| F | F | Cl | " | " | " | H | 158–159 |
| F | F | H | H | —SCHF$_2$ | " | " | 191–192 |
| " | " | F | " | " | " | " | 172–173 |
| F | F | Br | H | —SCF$_2$CHF$_2$ | " | " | 138–139 |
| Cl | H | " | " | " | " | " | 130–131 |
| Cl | H | Me | H | " | " | " | 125–126 |
| Cl | H | H | Me | —SCF$_2$CHF$_2$ | " | " | 176–177 |
| F | F | H | Cl | " | H | Cl | 189–190 |
| Cl | H | " | " | " | " | " | 182 |
| F | F | H | Me | " | H | Me | 151–152 |
| Cl | H | " | " | " | " | " | 157–158 |
| F | F | Me | Me | " | H | H | 145–146 |
| Cl | H | " | " | " | " | " | 145–146 |
| F | F | H | Cl | " | H | Me | 158–159 |
| Cl | H | " | " | " | " | " | 160–161 |
| F | F | Cl | H | —SCF$_2$CHFCl | H | H | 133–134 |
| Cl | H | " | " | " | " | " | 136–137 |
| F | F | Br | H | " | H | H | 148–149 |
| Cl | H | " | " | " | " | " | 131–132 |
| F | F | Me | H | " | " | " | 120–121 |
| F | Cl | " | " | " | " | " | 131–132 |
| Cl | Cl | " | " | " | " | " | 148–148.5 |

TABLE 3-continued

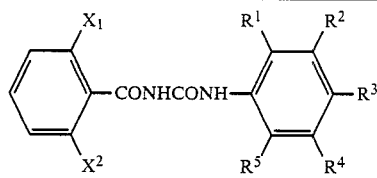

[II]

| $X^1$ | $X^2$ | $R^1$ | $R^2$ | $R^3$ | $R^4$ | $R^5$ | Melting point, °C. |
|---|---|---|---|---|---|---|---|
| Cl | H | " | " | " | " | " | 127.5–130 |
| Cl | H | Cl | Cl | " | " | " | 179–180 |
| F | F | H | Me | " | " | Me | 146–147 |
| Cl | H | " | " | " | " | " | 148–149 |
| F | F | Me | Me | " | H | H | 150–151 |
| Cl | H | " | " | " | " | " | 145–146 |
| F | F | H | Cl | " | H | Me | 157–159 |
| Cl | H | " | " | " | " | " | 173–174 |
| F | Cl | Cl | Cl | " | H | H | 177–178 |
| Cl | Cl | " | " | " | " | " | 176–178 |

*The parenthesized figures following the melting points indicate the content of impurities contained.

REFERENCE EXAMPLE 5

In 15 ml of toluene was dissolved 7.8 g of 2-fluoro-4-(1,1,2,2-tetrafluoroethylthio)aniline, and 4.0 g of acetic anhydride at 80° C. for 30 minutes, and concentrated to dryness under reduced pressure to give 2-fluoro-4-(1,1,2,2-tetrafluoroethylthio)acetanilide. Yield of 8.6 g, m.p. of 106°–107° C.

8.6 g of the above obtained crystals was dissolved in 15 ml of acetic acid, and 5 ml of 30% hydrogen peroxide was added to the solution, followed by heating at 70° C. for 4 hours. The reaction solution was diluted with water, and the crystals, which separated out, were recovered by filtration, and washed with water and a small amount of ethanol successively to give 5.6 g of 2-fluoro-4-(1,1,2,2-tetrafluoroethylsulfinyl)acetanilide.

3.2 g of the above crystals was dissolved in 50 ml of conc. hydrochloric acid, and the solution was heated under reflux for 1 hour, followed by concentration to dryness. 10% sodium hydroxide aqueous solution was added to the residue to make the mixture alkaline, followed by extraction with toluene. The toluene layer was dehydrated with anhydrous magnesium sulfate and concentrated to dryness under reduced pressure to give 2-fluoro-4-(1,1,2,2-tetrafluoroethylsulfinyl)aniline. Yield of 2.8 g, m.p. of 67°–69° C. after recrystallization from n-hexane.

By the procedure similar to Reference Example 5 the following anilines were synthesized.

2-Chloro-4-(1,1,2,2-tetrafluoroethylsulfinyl)aniline, melting point of 55° C.

2-Chloro-4-(1,1,2-trifluoro-2-chloroethylsulfinyl)aniline, melting point at 67° C.

4-(1,1,2-Trifluoro-2-chloroethylsulfinyl)aniline, melting point of 50° C.

REFERENCE EXAMPLE 6

In 50 ml of toluene was dissolved 26 g of 2-chloro-4-(1,1,2-trifluoro-2-chloroethylthio)aniline, and 13 g of acetic anhydride was added to the solution. The reaction solution was heated at 80° C. for 30 minutes and concentrated to dryness under reduced pressure, and the resulting crystals were washed with n-hexane to give 2-chloro-4-(1,1,2-trifluoro-2-chloroethylthio)acetanilide. Yield of 28.1 g, melting point of 77°–79° C.

3.2 g of the above crystals was dissolved in 20 ml of toluene, and 5.0 g of m-chloroperbenzoic acid was added little by little to the solution. The mixture was heated at 60° to 65° C. for 30 minutes with stirring, and concentrated to dryness under reduced pressure, and the resulting crystals were washed with 10% NaOH aqueous solution and water successively in the mentioned order to give 2-chloro-4-(1,1,2-trifluoro-2-chloroethylsulfonyl)acetanilide. Yield of 2.7 g, melting point of 124°–125° C.

2.5 g of the above crystals was added to 50 ml of conc. hydrochloric acid, and the mixture was heated under reflux for 2 hours, and concentrated to dryness under reduced pressure. The resulting crystals were washed with 10% NaOH aqueous solution and water successively in the mentioned order to give 2-chloro-4-(1,1,2-trifluoro-2-chloroethylsulfonyl)aniline. Yield of 2.0 g, melting point of 98°–99° C.

REFERENCE EXAMPLE 7

In 300 ml of dimethylformamide was dissolved 55 g of thiophenol, and 55 g of triethylamine was added to the solution. Trifluorochloroethylene was passed into the mixture over the period of 2 hours under heating with stirring at 60° C. (trifluorochloroethylene was generated by reacting 187 g of 1,1,2-trifluorotrichloroethane with 130 g of powdered zinc in ethanol in accordance with the conventional method). After the conclusion of the reaction, the reaction mixture was concentrated to dryness under reduced pressure, and the resulting oily material was distilled under reduced pressure to give 55 g of (1,1,2-trifluoro-2-chloroethyl)phenylsulfide as a colorless liquid having a boiling point of 52°–53° C./0.2 mmHg.

REFERENCE EXAMPLE 8

In 150 ml of acetic acid was dissolved 45 g of (1,1,2-trifluoro-2-chloroethyl)phenylsulfide, and 56 g of 30% hydrogen peroxide aqueous solution was added to the solution, followed by heating at 70° to 80° C. for 5 hours with stirring. The reaction mixture was concentrated under reduced pressure, and the concentrate was diluted with water, followed by extraction with carbon tetrachloride. The carbon tetrachloride extract was washed with water, dehydrated with anhydrous magnesium sulfate and concentrated to dryness under reduced pressure to give 51 g of (1,1,2-trifluoro-2-chloroethyl)-phenylsulfone as colorless crystals having a melting point of 38° to 39° C.

REFERENCE EXAMPLE 9

In 40 ml of conc. sulfuric acid was dissolved 40 g of (1,1,2-trifluoro-2-chloroethyl)phenylsulfone, and the solution was cooled to 0° C. A solution of 20 g of 70% nitric acid in 20 ml of conc. sulfuric acid was added dropwise to the solution over the period of 30 minutes. After the completion of the addition, the reaction mixture was stirred at room temperature (20° to 25° C.) for 2 hours, and poured into ice-cold water, followed by extraction with chloroform. The chloroform extract was washed with water, dehydrated with anhydrous magnesium sulfate and concentrated under reduced pressure. The resulting oily material was isolated and purified by silica gel column chromatography (solvent: dichloromethane) to give 19 g of a yellowish oily material.

18 g of the above oily material was dissolved in 50 ml of acetic acid, and 2 g of palladium-carbon catalyst was added to the solution, followed by catalytic reduction. The catalyst was filtered out, and the filtrate was concentrated to dryness under reduced pressure. The resulting residue was isolated and purified by silica-gel column chromatography (solvent: dichloromethane) to give 13.8 g of 3-(1,1,2-trifluoro-2-chloroethylsulfonyl)aniline, m.p. of 66°–67.5° C.

In accordance with the procedures as described in Reference Examples 7 through 9, the following compounds were synthesized.

3-(1,1,2,2-Trifluoroethylsulfonyl)aniline, b.p. of 140°–143° C./1–2 mmHg.

4-Chloro-3-(1,1,2,2-tetrafluoroethylsulfinyl)aniline, m.p. of 71°–72° C.

4-Chloro-3-(1,1,2-trifluoro-2-chloroethylsulfinyl)aniline, m.p. of 123°–124° C.

REFERENCE EXAMPLE 10

In 300 ml of water was dissolved 64.5 g of sodium hydroxide, and 100 g of 4-nitrothiophenol and 500 ml of dioxane were added to the solution. 112.5 g of chlorodifluoromethane was blown into the mixture under heating at 70° C. with stirring, and no absorption took place. The reaction mixture was cooled (20° C.), and extracted with toluene. The toluene layer was washed with water, 10% NaOH aqueous solution and water successively in the mentioned order, and dehydrated with anhydrous magnesium sulfate. The toluene layer was concentrated to dryness under reduced pressure, and distilled under reduced pressure to give 81.4 g of 4-difluoromethylthionitrobenzene, b.p. of 91°–95° C./0.5 mmHg.

REFERENCE EXAMPLE 11

To 300 ml of water were added 66 g of reduced iron and 12.1 g of conc. hydrochloric acid, and after the mixture was heated at 80° C. for 1 hour with stirring, 55.9 g of 4-difluoromethylthionitrobenzene was added dropwise to the mixture over the period of 30 minutes. The reaction mixture was heated at the same temperature for 2 hours with stirring, and 12.1 g of sodium carbonate was added gradually, followed by heating at 80° C. for another 1 hour with stirring. The insoluble matter was filtered out, and the filtrate was extracted with toluene. The toluene layer was washed with water, dehydrated with anhydrous magnesium sulfate, and concentrated under reduced pressure. The concentrate was distilled under reduced pressure to give 52.8 g of 4-difluoromethylthioaniline, b.p. of 90°–92° C./0.5 mmHg.

REFERENCE EXAMPLE 12

In 20 ml of methanol was dissolved 18.4 g of 2-fluoro-4-mercaptoaniline hydrochloride, and after the solution was cooled to 0° C., 39.4 g of 28% sodium methylate solution was added dropwise to it. 30 minutes later, the insoluble matter was filtered out, the filtrate was concentrated to dryness under reduced pressure. 200 ml of dioxane was added to the residue, and 23 g of chlorodifluoromethane was blown into the mixture under heating at 50° C. with stirring, followed by cooling (20° C.) and extraction with toluene. The toluene extract was washed with water, dehydrated with anhydrous magnesium sulfate, and concentrated to dryness under reduced pressure, followed by distillation to give 11.5 g of 2-fluoro-4-difluoromethylthio-aniline, b.p. of 65°–67° C./0.2 mmHg.

EXAMPLE 1

To a solution of 0.7 g of 2-fluoro-4-(1,1,2,2-tetrafluoroethylsulfinyl)aniline in 15 ml of toluene was added 0.5 g of 2-fluoro-6-chlorobenzoyl isocyanate. After the reaction was allowed to proceed at room temperature (20° to 25° C.) for 30 minutes, the crystals which separated out were recovered by filtration and washed with toluene to give 1.0 g of N-(2-fluoro-6-chlorobenzoyl)-N'-[2-fluoro-4-(1,1,2,2-tetrafluoroethylsulfinyl)phenyl]urea (Compound No. 31), m.p. of 213°–216° C.

Elemental analysis, for $C_{16}H_9N_2F_6ClO_3S.1/10$ toluene Calcd.: C, 42.86%; H, 2.11%; N, 5.99%; Found: C, 42.83%; H, 2.07%; N, 6.02%.

EXAMPLE 2

In a mixed solution consisting of 5 ml of acetic acid and 10 ml of trifluoroacetic acid was dissolved under heating 0.6 g of N-(2-fluoro-6-chlorobenzoyl)-N'-[2-fluoro-4-(1,1,2,2-tetrafluoroethylsulfinyl)phenyl]urea, and 1.5 ml of 30% hydrogen peroxide aqueous solution was added to the solution, followed by heating at 90° C. for 2 hours. The reaction mixture was diluted with water, and the crystals which separated out were recovered by filtration, and washed with water and ethanol successively to give 0.6 g of N-(2-fluoro-6-chlorobenzoyl)-N'-[2-fluoro-4-(1,1,2,2-tetrafluoroethylsulfonyl)phenyl]urea (Compound No. 6), m.p. of 176°–177° C.

Elemental analysis, for $C_{16}H_9N_2F_6ClO_4S$ Calcd.: C, 40.48%; H, 1.91%; N, 5.50%; Found: C, 40.50%; H, 18.83%; N, 5.84%.

EXAMPLE 3

In 20 ml of acetic acid was dissolved under heating 0.4 g of N-(2,6-difluorobenzoyl)-N'-[2,5-dichloro-4-(1,1,2,2-tetrafluoroethylthio)phenyl]urea, and 1 ml of 30% hydrogen peroxide aqueous solution was added to the solution, followed by heating at 90° C. for 3.5 hours. The reaction mixture was diluted with water, and the crystals which separated out were recovered by filtration, and washed with water and ethanol successively to give 0.4 g of N-(2,6-difluorobenzoyl)-N'-[2,5-dichloro-4-(1,1,2,2-tetrafluoroethylsulfinyl)phenyl]urea (Compound No. 34), m.p. of 216°–220° C.

Elemental analysis, for $C_{16}H_8N_2F_6Cl_2O_3S$ Calcd.: C, 38.96%; H, 1.63%; N, 5.68%; Found: C, 38.88%; H, 1.59%; N, 5.63%.

EXAMPLE 4

In 20 ml of acetic acid was dissolved under heating 0.6 g of N-(2,6-difluorobenzoyl)-N'-[2-fluoro-4-(1,1,2,2-tetrafluoroethylthio)phenyl]urea, and 5 ml of 30% hydrogen peroxide aqueous solution was added to the solution, followed by heating at 65° C. for 4 hours. The reaction mixture was diluted with water, and the crystals which separated out were recovered by filtration, and washed with water to give 0.6 g of N-(2,6-difluorobenzoyl)-N'-[2-fluoro-4-(1,1,2,2-tetrafluoroethylsulfonyl)phenyl]urea (Compound No. 5), m.p. of 186°–187° C.

Elemental analysis, for $C_{16}H_9N_2F_7O_4S$ Calcd.: C, 41.93%; H, 1.98%; N, 6.11%; Found: C, 42.13%; H, 1.89%; N, 6.09%.

EXAMPLE 5

In 20 ml of toluene was dissolved 20 g of 3-(1,1,2-trifluoro-2-chloroethylsulfonyl)aniline, amd 1.4 g of 2,6-difluorobenzoyl isocyanate was added to the solution, followed by stirring at room temperature (20° to 25° C.) for 2 hours. The reaction mixture was concentrated under reduced pressure, and the crystals which separated out were recovered by filtration, and washed with cyclohexane to give 3.3 g of N-(2,6-difluorobenzoyl)-N'-(3-(1,1,2-trifluoro-2-chloroethylsulfonyl)phenyl]urea (Compound No. 38), m.p. of 192°–194° C.

Elemental analysis, for $C_{16}H_9N_2F_5ClO_4S$ Cacld.: C, 42.07%; H, 2.09%; N, 6.13%; Found: C, 41.92%; H, 2.24%; N, 5.86%.

EXAMPLE 6

To 4% phosgen-toluene solution was added 4.0 g of 2-fluoro-4-(1,1,2,2-tetrafluoroethylsulfonyl)aniline, followed by heating under reflux for 3 hours. After the completion of the reaction, the reaction mixture was concentrated to dryness under reduced pressure to give 2-fluoro-4-(1,1,2,2-tetrafluoroethylsulfonyl)phenyl isocyanate as an oily material. In 50 ml of xylene was dissolved the oily material, and 1.5 of 2.6-difluorobenzamide was added to the solution, followed by heating under reflux for 20 hours. After the completion of the reaction, the reaction mixture was cooled to 0° C., and the crystals which separated out was recovered by filtration and recrystallized from acetone to give N-(2,6-difluorobenzoyl)-N'-[2-fluoro-4-(1,1,2,2-tetrafluoroethylsulfonyl)phenyl]urea (Compound No. 5) as crystals having a melting point of 186°–187° C. The melting point of the crystals did not descend in a mixed examination with the product of Example 4.

By the procedures similar to the above Examples, the compounds [I] as shown in the below Table were synthesized. The results are tabulated in Table 4, in which the compounds produced in Examples 1 through 5 are included.

TABLE 4

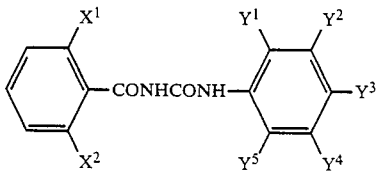

[I]

| Com'd No. | $X^1$ | $X^2$ | $Y^1$ | $Y^2$ | $Y^3$ | $Y^4$ | $Y^5$ | Melting point, °C. |
|---|---|---|---|---|---|---|---|---|
| 1 | F | F | H | H | $SO_2CF_2CHF_2$ | H | H | 196–197 |
| 2 | " | Cl | " | " | " | " | " | 191–192 |
| 3 | Cl | " | " | " | " | " | " | 211–213.5 |
| 4 | " | H | " | " | " | " | " | 180–182 (1/7 acetone)** |
| 5 | F | F | F | " | " | " | " | 186–187 |

TABLE 4-continued

| Com'd No. | X¹ | X² | Y¹ | Y² | Y³ | Y⁴ | Y⁵ | Melting point, °C. |
|---|---|---|---|---|---|---|---|---|
| 6 | " | Cl | " | " | " | " | " | 176–177 |
| 7 | Cl | " | " | " | " | " | " | 184–185 |
| 8 | " | H | " | " | " | " | " | 188–189 |
| 9 | F | F | Cl | " | " | " | " | 187–188 |
| 10 | Cl | H | " | " | " | " | " | 159–160 |
| 11 | F | F | Me | " | " | " | " | 171–173 |
| 12 | " | " | H | Cl | " | " | " | 195–198 |
| 13 | Cl | H | " | " | " | " | " | 178–179 |
| 14 | F | F | " | Me | " | " | " | 195–197 |
| 15 | " | " | " | Cl | " | " | Cl | 188 |
| 16 | Cl | H | " | " | " | " | " | 214–217 |
| 17 | F | F | Cl | " | " | " | H | 194–195 |
| 18 | Cl | H | " | " | " | " | " | 164–166 |
| 19 | F | F | H | " | " | Cl | " | 202 |
| 20 | " | " | " | " | " | H | F | 207–209 |
| 21 | Cl | H | H | Cl | SO₂CF₂CHF₂ | H | F | 216–218 |
| 22 | F | F | " | H | SO₂CF₂CHFCl | " | H | 210–211 |
| 23 | " | Cl | " | " | " | " | " | 196–197 |
| 24 | Cl | " | " | " | " | " | " | 217–218 |
| 25 | " | H | " | " | " | " | " | 172–173 |
| 26 | F | F | F | " | " | " | " | 190 |
| 27 | Cl | H | " | " | " | " | " | 195 |
| 28 | F | F | H | Cl | " | " | Cl | 191–193 |
| 29 | Cl | H | " | " | " | " | " | 211–213 |
| 30 | F | F | F | H | —SOCF₂CHF₂ | " | H | 209–211 |
| 31 | " | Cl | " | " | " | " | " | 213–216 (1/10 toluene)** |
| 32 | Cl | " | " | " | " | " | " | 240–241 |
| 33 | " | H | " | " | " | " | " | 176–179 |
| 34 | F | F | H | Cl | " | " | Cl | 216–220 |
| 35 | " | " | Cl | " | —SOCF₂CHFCl | " | H | 188–189 |
| 36 | F | F | H | H | SO₂CHF₂ | H | H | 208–210 |
| 37 | " | " | F | " | " | " | " | 208–210 |
| 38 | " | " | H | H | H | SO₂CF₂CHFCl | " | 192–194 |
| 39 | " | Cl | " | " | " | " | " | 153–154 |
| 40 | Cl | " | " | " | " | " | " | 186–187 |
| 41 | " | H | " | " | " | " | " | 137–138 |
| 42 | F | F | H | H | H | SO₂CF₂CHF₂ | H | 193–194 |
| 43 | " | Cl | " | " | " | " | " | 174–175 |
| 44 | Cl | " | " | " | " | " | " | 189–190 |
| 45 | Cl | H | " | " | " | " | " | 137–138 |
| 46 | F | F | " | " | Cl | SOCF₂CHF₂ | " | 194–195 |
| 47 | F | Cl | H | H | Cl | SOCF₂CHF₂ | H | 187–188 |
| 48 | Cl | " | " | " | " | " | " | 196–197 |
| 49 | " | H | " | " | " | " | " | 164–165 |
| 50 | F | F | " | " | " | SOCF₂CHFCl | " | 226–227 |
| 51 | " | Cl | " | " | " | " | " | 176–177 |
| 52 | Cl | " | " | " | " | " | " | 194–195 |
| 53 | " | H | " | " | " | " | " | 180–181 |
| 54 | Cl | " | Me | " | SO₂CF₂CHF₂ | H | " | 169.5–171.5 |
| 55 | F | F | Br | " | " | " | " | 184–185 |
| 56 | Cl | H | " | " | " | " | " | 171–172 |
| 57 | Cl | H | H | Me | " | " | " | 177–178 |
| 58 | F | F | Me | H | " | Me | H | 159–160 |
| 59 | Cl | H | " | " | " | " | " | 197–198 |
| 60 | F | F | Me | Me | " | H | " | 181–182 |
| 61 | Cl | H | " | " | " | " | " | 159–160 |
| 62 | F | F | Me | H | " | Cl | " | 186–188 |
| 63 | Cl | H | " | " | " | " | " | 202–204 |
| 64 | F | F | Cl | " | SO₂CF₂CHFCl | H | " | 183–184 |
| 65 | Cl | H | " | " | " | " | " | 160–161 |
| 66 | F | F | Br | " | " | " | " | 183–184 |
| 67 | Cl | H | " | " | " | " | " | 154–155 |
| 68 | F | F | Me | " | " | " | " | 161–162 |
| 69 | " | Cl | " | " | " | " | " | 174–175.5 |
| 70 | Cl | " | " | " | " | " | " | 189–190 |
| 71 | Cl | H | " | " | " | " | " | 157–158 |
| 72 | F | F | Cl | Cl | " | " | " | 186.5–187.5 |
| 73 | F | F | Me | H | SO₂CF₂CHFCl | Me | H | 175–176 |
| 74 | Cl | H | " | " | " | " | " | 190–191 |
| 75 | F | F | Me | Me | " | H | " | 185–186 |

TABLE 4-continued $$\text{[I]}$$

Structure: 2,6-disubstituted(X¹,X²) benzoyl-CONHCONH-phenyl(Y¹,Y²,Y³,Y⁴,Y⁵)

| Com'd No. | X¹ | X² | Y¹ | Y² | Y³ | Y⁴ | Y⁵ | Melting point, °C. |
|---|---|---|---|---|---|---|---|---|
| 76 | Cl | H | " | " | " | H | " | 175–176 |
| 77 | F | F | Me | H | SO₂CF₂CHFCl | Cl | H | 183–184 |
| 78 | Cl | H | " | " | " | " | " | 198–199 |
| 79 | F | F | H | H | —SOCF₂CHFCl | H | H | 212 |
| 80 | Cl | H | " | " | " | " | " | 183 (1/20 toluene)** |
| 81 | F | F | Cl | " | —SOCF₂CHF₂ | " | " | 216–217 |
| 82 | Cl | H | " | " | " | " | " | 181–182 (1/10 toluene)** |
| 83 | Cl | H | Me | " | " | " | " | 151–153 |
| 84 | Cl | H | H | Cl | " | " | Cl | 214–215 |
| 85 | F | F | Cl | H | —SOCF₂CHFCl | H | H | 205 (1/15 toluene)** |
| 86 | Cl | H | " | " | " | " | " | 165 |
| 87 | F | F | H | Cl | " | " | Cl | 212–214 |
| 88 | Cl | H | " | " | " | " | " | 201–202 |
| 89 | F | Cl | Cl | Cl | " | " | H | 200–202 |
| 90 | Cl | Cl | " | " | " | " | H | 209–210 |
| 91 | Cl | H | " | " | " | " | H | 185–188 |
| 92 | F | F | " | " | —SOCF₂CHF₂ | " | " | 196 |
| 93 | Cl | H | " | " | " | " | " | 186–188 |
| 94 | Cl | Cl | " | " | " | " | " | 208 |
| 95 | F | F | Me | Me | " | H | H | 197–198 |
| 96 | Cl | H | " | " | " | " | " | 172–174 |
| 97 | F | F | Me | H | " | Me | H | 173–174 |
| 98 | Cl | H | " | " | " | " | " | 186–188 |
| 99 | F | F | Me | Me | —SOCF₂CHFCl | H | H | 187–188 |
| 100 | Cl | H | " | " | " | " | " | 184–185 |
| 101 | F | F | Me | H | " | Me | H | 188–189 |
| 102 | Cl | H | " | " | " | " | " | 193–194 |
| 103 | Cl | H | Cl | Cl | —SO₂CF₂CHFCl | H | H | 152–153 |
| 104 | F | F | F | H | —SOCF₂CHFCl | H | H | 175–177 |
| 105 | Cl | H | " | " | " | " | " | 176–177 |
| 106 | F | F | Me | " | " | " | " | 148–149 |
| 107 | Cl | H | " | " | " | " | " | 153–156 |
| 108 | F | F | Me | " | —SOCF₂CHF₂ | " | " | 176–176.5 |
| 109 | F | Cl | Cl | Cl | " | " | " | 185–188 |

**The parenthesized figures following the melting points indicate the content of impurities contained; Me denotes a methyl group.

EXAMPLE 7

| (Emulsifiable concentrate) | |
|---|---|
| Compound No. 5 | 20 weight % |
| Dimethylformamide | 75 weight % |
| Polyoxyethylene glycol ether (Nonipol 85 ®, produced by Sanyo Chemical Ind. of Japan) | 5 weight % |

An emulsifiable concentrate formed by mixing the above ingredients (to be sprayed after diluting with water to a desired concentration on the occasion of use).

EXAMPLE 8

| (Wettable powder) | |
|---|---|
| Compound No. 8 | 25 weight % |
| Polyoxyethylene glycol ether (Nonipol 85 ®, produced by Sanyo Chemical Ind. of Japan) | 6 weight % |
| Diatomaceous earth | 69 weight % |

A wettable powder formed by mixing the above ingredients (to be sprayed after diluting with water to a desired concentration on the occasion of use).

EXAMPLE 9

| (Wettable powder) | |
|---|---|
| Compound No. 26 | 25 weight % |
| Sodium lignin sulfonate | 5 weight % |
| Polyoxyethylene glycol ether (Nonipol-85 ®, produced by Sanyo Chemical Ind. of Japan) | 5 weight % |
| Clay | 65 weight % |

A wettable powder formed by uniformly mixing and pulverizing the above ingredients (to be sprayed after diluting with water to a desired concentration on the occasion of use).

EXAMPLE 10

| (Powder) | |
|---|---|
| Compound No. 27 | 10 weight % |
| Clay | 89.3 weight % |

-continued

| (Powder) | |
|---|---|
| Silicone | 0.5 weight % |
| Polyethylene glycol ether | 0.2 weight % |

A powder formed by uniformly mixing and pulverizing the above ingredient.

EXAMPLE 11

| (Granule) | |
|---|---|
| Compound No. 5 | 5 weight % |
| Clay | 72 weight % |
| Bentonite | 20 weight % |
| Polyoxyethylene glycol ether (Nonipol 85 ®, produced by Sanyo Chemical Ind. of Japan) | 0.5° weight % |
| Sodium carboxymethyl cellulose | 2.5 weight % |

The above ingredients were uniformly mixed and pulverized, and water of 8 weight % against the total weight was added to the mixture, followed by kneading. Subsequently, the mixture was processed into granules, which were dried to a granule preparation, in accordance with the conventional method.

EXAMPLE 12

| (Granule) | |
|---|---|
| Compound No. 8 | 2 weight % |
| Sodium lignin sulfonate | 5 weight % |
| Bentonite | 93 weight % |

A mixture of the above ingredients was uniformly mixed and pulverized, and water of 10 weight % against the total weight was added to the mixture, followed by kneading. Subsequently, the mixture was processed into granules, which were dried to a granule preparation, in accordance with the conventional method.

TEST EXAMPLE 1

Insecticidal effect against *Spodoptera litura*

A test compound was processed into an emulsifiable concentrate in accordance with the same formulation as described in Example 7, and diluted with water to prepare treatment solutions (admixed with 0.03% of Spreader Dain ®, produced by Takeda Chemical Industries, Ltd. of Japan) of 2 and 10 ppm. 20 ml each of the treatment solutions were sprayed on soybean seedlings (14 days after germination) grown in a pot in a spray chamber with use of a spray gun (with a spraying pressure of 1 kg/cm²). One day after spraying, two treated leaves were cut off, and placed in an ice-cream cup (with a diameter of 6 cm and a depth of 4 cm), in which 10 third-instar larvae of *Spodoptera litura* were released. After releasing, the above cup was placed in a room (25° C.), and examined for a number of dead larvae 4 days later. The test was repeated twice, whereby the test results were expressed in terms of rate of death (%) as shown in Table 5.

TEST EXAMPLE 2

Insecticidal effect against *Plutella xylostella*

In accordance with the same formulation and preparation method as described in Test Example 1, there were prepared 3.3 and 10 ppm treatment solutions of a test compound, and 20 ml each of the treatment solutions were sprayed on seedlings (25 days after germination) of Hatsuka-daikon (a kind of radish) grown in a pot by the same spraying procedure as in Test Example 1. 2 hours after spraying, two treated leaves were cut off and placed in an ice-cream cup, in which 10 second-instar larvae of *Plutella xylostella* were released. After releasing, the above cup was placed in a room, and examined for a number of dead larvae 4 days later. The test was repeated twice, whereby the test results were expressed in terms of rate of death (%) as shown in Table 6.

TEST EXAMPLE 3

Insecticidal effect against *Adoxophyes orana*

In accordance with the same formulation as described in Example 9, a test compound was processed into a wettable powder, and the wettable powder was diluted with water to prepare 5 and 20 ppm treatment solutions (admixed with 0.03% of Spreader Dain ®). The whole leaves of soybean seedlings (14 days after germination) grown in a pot were immersed in each of the treatment solutions for 10 seconds and air-dried, and two leaves thus treated were cut off and placed in an ice-cream cup, in which 10 second-instar larvae of *Adoxophyes orana* were released. After releasing, the above cup was placed in a room (25° C.) and examined for a number of dead larvae 7 days later. The test was repeated twice, whereby the test results were expressed in terms of rate of death (%) as shown in Table 7.

TEST EXAMPLE 4

Insecticidal effect against *Henosepilachna vigintioctopunctata*

In accordance with the same formulation and preparation method as described in Test Example 1, 4 and 20 ppm treatment solutions of a test compound were prepared. A cut piece (5 mm thick) of a potato was immersed in each of the treatment solutions for 10 seconds, air-dried and transferred into a Petri dish (with a diameter of 9 cm), in which 10 second-instar larvae of *Henosepilachna Viginitioctopunctata* were released. After releasing, the Petri dish was placed in a room (25° C.) and examined for a number of dead larvae 7 days later. The test was repeated twice, whereby the test results were expressed in terms of rate of death (%) as shown in Table 8.

In the respective tests mentioned above, the following compounds were used as a control compound:
Control compound A=Dimilin:
N-(4-Chlorophenyl)-N'-(2,6-difluorobenzoyl)urea (Diflubenzuron)

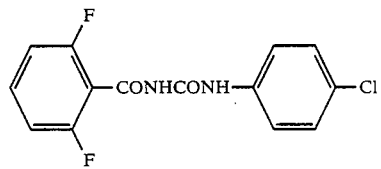

Control compound B=Acephate
N-Acetylphosphoramidothiol acid, O,S-dimethyl.

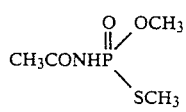

Control compound C = the compound of European patent publication No. 71279.

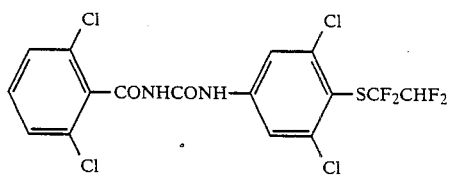

TABLE 5

| Comp'd. No. | Spodoptera litura rate of death (%) | |
|---|---|---|
| | 2 ppm | 10 ppm |
| 2 | — | 100 |
| 3 | — | 100 |
| 5 | 100 | 100 |
| 6 | " | " |
| 7 | " | " |
| 8 | " | " |
| 9 | " | " |
| 10 | " | " |
| 11 | " | " |
| 12 | — | " |
| 13 | 100 | " |
| 14 | — | " |
| 15 | 100 | " |
| 16 | " | " |
| 17 | " | " |
| 18 | " | " |
| 19 | — | 100 |
| 20 | 100 | " |
| 21 | " | " |
| 23 | 95 | 100 |
| 24 | 95 | " |
| 25 | — | " |
| 26 | 100 | 100 |
| 27 | " | " |
| 28 | " | " |
| 29 | " | " |
| 30 | " | " |
| 31 | " | " |
| 32 | " | " |
| 33 | " | " |
| 34 | 100 | 100 |
| 35 | 100 | 100 |
| 37 | 100 | 100 |
| 54 | 100 | 100 |
| 55 | " | " |
| 56 | " | " |
| 57 | " | " |
| 58 | " | " |
| 59 | 95 | " |
| 60 | 100 | " |
| 61 | " | " |
| 62 | " | " |
| 63 | " | " |
| 64 | " | " |
| 65 | " | " |
| 66 | " | " |
| 67 | " | " |
| 68 | 100 | 100 |
| 69 | " | " |
| 70 | — | " |
| 71 | 100 | " |
| 72 | " | " |
| 73 | " | " |
| 74 | " | " |
| 75 | " | " |
| 76 | " | " |

TABLE 5-continued

| Comp'd. No. | Spodoptera litura rate of death (%) | |
|---|---|---|
| | 2 ppm | 10 ppm |
| 77 | " | " |
| 78 | " | " |
| 91 | — | " |
| 92 | 100 | " |
| 93 | " | " |
| 94 | — | " |
| 95 | 100 | " |
| 96 | " | " |
| 97 | " | " |
| 98 | 100 | 100 |
| 99 | " | " |
| 100 | " | " |
| 101 | " | " |
| 102 | " | " |
| 104 | " | " |
| 105 | " | " |
| 106 | " | " |
| 107 | " | " |
| 108 | " | " |
| 109 | " | " |
| control compound A | 10 | 95 |
| control compound B | 0 | 0 |
| Control compound C | 30 | — |
| none | 0 | 0 |

TABLE 6

| Comp'd. No. | Plutella xylostella (%) rate of death | |
|---|---|---|
| | 3.3 ppm | 10 ppm |
| 1 | 90 | 100 |
| 2 | 100 | " |
| 5 | 100 | 100 |
| 6 | " | " |
| 7 | — | 90 |
| 8 | 100 | 100 |
| 9 | 95 | " |
| 10 | — | 95 |
| 11 | 100 | 100 |
| 12 | — | " |
| 13 | — | 95 |
| 14 | 100 | 100 |
| 15 | 95 | " |
| 17 | 95 | 100 |
| 18 | 100 | " |
| 19 | 90 | " |
| 20 | 100 | " |
| 21 | — | |
| 23 | 100 | 100 |
| 24 | " | " |
| 25 | " | " |
| 26 | " | " |
| 27 | " | " |
| 28 | " | " |
| 29 | " | " |
| 30 | " | " |
| 31 | " | " |
| 32 | — | 95 |
| 33 | 100 | 100 |
| 34 | 100 | 100 |
| 35 | 100 | 100 |
| 37 | — | 100 |
| 54 | — | 90 |
| 55 | — | 100 |
| 57 | 100 | 100 |
| 58 | " | " |
| 60 | " | " |
| 61 | " | " |
| 62 | " | " |
| 63 | — | 90 |
| 64 | 95 | 100 |
| 65 | 100 | " |

TABLE 6-continued

| Comp'd. No. | Plutella xylostella (%) rate of death | |
|---|---|---|
| | 3.3 ppm | 10 ppm |
| 66 | — | 95 |
| 67 | — | 100 |
| 68 | 100 | " |
| 69 | " | " |
| 70 | — | 100 |
| 71 | 95 | 100 |
| 72 | 100 | " |
| 73 | " | " |
| 74 | " | " |
| 75 | " | " |
| 76 | " | " |
| 77 | 100 | 100 |
| 78 | — | " |
| 91 | — | " |
| 92 | 100 | " |
| 93 | — | " |
| 94 | 90 | " |
| 95 | 100 | " |
| 96 | 90 | " |
| 97 | 100 | " |
| 98 | 90 | " |
| 99 | 100 | " |
| 100 | " | " |
| 101 | 100 | " |
| 102 | " | " |
| 104 | " | " |
| 105 | " | " |
| 106 | " | " |
| 107 | " | " |
| 108 | " | " |
| 109 | " | " |
| Control compound A | 0 | 5 |
| Control compound B | 0 | 0 |
| Control compound C | — | 15 |
| none | 0 | 0 |

TABLE 7

| Comp'd. No. | Adoxophyes orana rate of death (%) | |
|---|---|---|
| | 5 ppm | 20 ppm |
| 2 | 100 | 100 |
| 3 | 100 | 100 |
| 4 | — | 100 |
| 5 | 100 | 100 |
| 7 | 100 | 100 |
| 8 | 95 | 100 |
| 9 | 100 | " |
| 10 | — | " |
| 11 | 100 | " |
| 12 | " | " |
| 13 | — | " |
| 15 | 90 | 100 |
| 17 | 100 | 100 |
| 18 | 100 | 100 |
| 19 | — | 100 |
| 20 | 100 | 100 |
| 23 | 100 | 100 |
| 24 | " | " |
| 25 | 95 | " |
| 26 | 100 | 100 |
| 27 | 95 | 100 |
| 28 | 100 | 100 |
| 29 | — | 100 |
| 30 | 100 | 100 |
| 31 | 100 | 100 |
| 34 | — | 100 |
| 35 | 100 | 100 |
| 37 | — | 100 |
| 54 | — | 100 |
| 58 | 95 | 100 |
| 60 | 100 | 100 |

TABLE 7-continued

| Comp'd. No. | Adoxophyes orana rate of death (%) | |
|---|---|---|
| | 5 ppm | 20 ppm |
| 61 | 95 | 100 |
| 62 | 90 | 100 |
| 64 | 100 | 100 |
| 65 | — | 100 |
| 66 | 90 | 100 |
| 67 | 90 | 100 |
| 68 | 100 | 100 |
| 69 | 100 | 100 |
| 70 | 90 | 100 |
| 71 | 90 | 100 |
| 72 | 100 | 100 |
| 73 | 100 | 100 |
| 74 | — | 100 |
| 75 | 100 | 100 |
| 76 | 100 | 100 |
| 77 | 100 | 100 |
| 80 | — | 100 |
| 85 | 95 | 100 |
| 86 | 95 | 100 |
| 87 | 100 | 100 |
| 88 | 90 | 100 |
| 89 | — | 100 |
| 90 | 100 | 100 |
| 92 | 90 | 100 |
| 93 | — | 100 |
| 94 | 100 | 100 |
| 95 | 90 | 100 |
| 96 | 100 | 100 |
| 97 | 100 | 100 |
| 98 | 100 | 100 |
| 99 | 100 | 100 |
| 100 | 100 | 100 |
| 101 | 100 | 100 |
| 102 | 90 | 100 |
| 104 | 100 | 100 |
| 105 | 90 | 100 |
| 106 | 100 | 100 |
| 107 | 90 | 100 |
| 108 | 100 | 100 |
| 109 | 90 | 100 |
| Control compound A | 0 | 0 |
| Control compound B | 0 | 0 |
| none | 0 | 0 |

TABLE 8

| Comp'd No. | Henosepilachna Vigintioctopunctata rate of death (%) | |
|---|---|---|
| | 4 ppm | 20 ppm |
| 2 | — | 95 |
| 3 | — | 100 |
| 5 | — | 95 |
| 7 | — | 95 |
| 8 | — | 95 |
| 10 | — | 95 |
| 14 | — | 95 |
| 15 | — | 95 |
| 16 | — | 95 |
| 17 | — | 95 |
| 19 | 95 | 95 |
| 20 | — | 95 |
| 26 | 100 | 100 |
| 27 | 100 | 100 |
| 34 | — | 90 |
| 35 | 95 | 95 |
| 55 | 100 | 100 |
| 65 | — | 100 |
| 68 | 100 | 100 |
| 69 | 95 | 100 |
| 70 | 95 | 95 |
| 71 | 95 | 100 |
| 72 | 100 | 100 |
| 76 | — | 95 |

TABLE 8-continued

| Comp'd No. | Henosepilachna Vigintioctopunctata rate of death (%) | |
|---|---|---|
| | 4 ppm | 20 ppm |
| 77 | — | 100 |
| 78 | — | 95 |
| 81 | 90 | 100 |
| 82 | 95 | 100 |
| 86 | 100 | 100 |
| 95 | 90 | 100 |
| 96 | 90 | 100 |
| 97 | 100 | 100 |
| 98 | 95 | 100 |
| 99 | 100 | 100 |
| 100 | 90 | 100 |
| 101 | 95 | 100 |
| 102 | 95 | 100 |
| 104 | — | 100 |
| 105 | 95 | 100 |
| 106 | — | 95 |
| 107 | 95 | 100 |
| 108 | 95 | 100 |
| 109 | 95 | 100 |
| Control compound A | 60 | 80 |
| Control compound B | 0 | 0 |
| Control compound C | — | 50 |
| none | 0 | 0 |

What we claim is:

1. A compound of the formula:

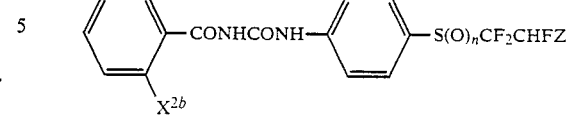

wherein n is 1 or 2; $X^{1b}$ is F or Cl; $X^{2b}$ is F or Cl, when $X^{1b}$ is F, or $X^{2b}$ is hydrogen or Cl, when $X^{1b}$ is Cl; $Y^{1d}$ is F, Cl, Br or methyl; and Z is F or Cl.

2. A compound as claimed in claim 1, which is N-(2,6-difluorobenzoyl)-N'-[2-fluoro-4-(1,1,2-trifluoro-2-chloroethylsulfonyl)phenyl]urea.

3. A compound as claimed in claim 1, which is N-(2-chlorobenzoyl)-N'-[2-fluoro-4-(1,1,2,2-tetrafluoroethylsulfonyl)phenyl]urea.

4. A compound as claimed claim 1, which is N-(2,6-difluorobenzoyl)-N'-[2-methyl-4-(1,1,2-trifluoro-2-chloroethylsulfonyl)phenyl]urea.

5. An insecticidal and/or ovicidal composition which contains an effective amount compound of the formula:

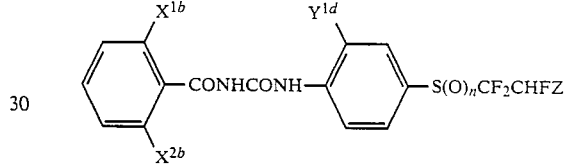

wherein n is 1 or 2; $X^{1b}$ is F or Cl; $X^{2b}$ is F or Cl, when $X^{1b}$ is F, or $X^{2b}$ is hydrogen or Cl, when $X_{1b}$ is Cl; $Y^{1d}$ is F, Cl, Br or methyl; and Z is F or Cl, and a suitable carrier or carriers.

* * * * *